(12) United States Patent
Bremberg et al.

(10) Patent No.: US 6,551,467 B1
(45) Date of Patent: Apr. 22, 2003

(54) MICROWAVE FACILITATED ALLYLLIC SUBSTITUTION

(75) Inventors: Ulf Bremberg, Solna (SE); Anders Hallberg, Uppsala (SE); Mats Larhed, Uppsala (DE); Christina Moberg, Täby (SE); Nils-Fredrik Kaiser, Uppsala (SE)

(73) Assignee: Personal Chemistry i Uppsala AB, Uppsala (SE)

( * ) Notice: Subject to any disclaimer, the term of this patent is extended or adjusted under 35 U.S.C. 154(b) by 0 days.

(21) Appl. No.: 09/786,199

(22) PCT Filed: Sep. 3, 1999

(86) PCT No.: PCT/IB99/01606

§ 371 (c)(1),
(2), (4) Date: Apr. 16, 2001

(87) PCT Pub. No.: WO00/14034

PCT Pub. Date: Mar. 16, 2000

(30) Foreign Application Priority Data

Sep. 4, 1998 (DK) .......................................... 1998 01119
Jun. 16, 1999 (DK) .......................................... 1999 00851

(51) Int. Cl.[7] .............................. C07F 5/00; C07F 9/02

(52) U.S. Cl. ............................... 204/157.6; 204/157.69; 204/157.7; 204/157.71; 204/157.72; 204/157.73; 204/157.76; 204/157.77; 204/157.78

(58) Field of Search .......................... 204/157.6, 157.69, 204/157.7, 157.71, 157.72, 157.73, 157.76, 157.77, 157.78

(56) References Cited

FOREIGN PATENT DOCUMENTS

WO          9743230          11/1997

OTHER PUBLICATIONS

Bremberg, Journal of Organic Chemistry, vol. 64, No. 4, pp. 1082–1083 (1999) no month available.

*Primary Examiner*—Edna Wong
(74) *Attorney, Agent, or Firm*—Birch, Stewart, Kolasch & Birch, LLP.

(57) ABSTRACT

The present invention is draw to microwave heating of a transition metal-catalysed organic reaction, in which a catalyst complex between a transition metal and an auxiliary ligand or ligands, the ligand being asymmetric or symmetric, monodentate or bidentate, results in highly chemoselective, regioselective, and stereoselective allylic substitution reactions. Molybdenum or palladium complexes form suitable catalytic systems with a plethora of ligands in a variety of solvents for such microwave facilitated nucleophilic substitution reactions.

57 Claims, 1 Drawing Sheet

MICROWAVE FACILITATED ALLYLLIC SUBSTITUTION

This application is the national phase under 35 U.S.C. §371 of PCT International Application No. PCT/IB99/01606 which has an International filing date of Sep. 3, 1999, which designated the United States of America.

The present invention relates to transition metal-catalysed organic reactions in general, preferably reactions occurring via allyl-metal-intermediates, in particular microwave heated very rapid highly selective (chemo-, regio- and stereo-) allylic substitutions utilising molybdenum or palladium together with an auxiliary ligand as catalytic system.

BACKGROUND OF THE INVENTION

Metal-catalysed asymmetric allylic substitution reactions have attracted considerable interest primarily due to their synthetic utility.[1,2] The enantioselectivity in the reaction is determined either during complex formation or, with substrates yielding meso-allyl ligands, at the nucleophilic attack on either of the two diastereotopic allyl-carbon atoms of the allyl-metal intermediate.[1,2] The absolute configuration of the starting material is not recognised in the intermediate allyl-metal complex and high asymmetric induction can be achieved by the employment of chiral ligands. A plethora of $C_1$- and $C_2$-symmetric chiral ligands are available for this reaction class,[3] and among these, multidentate ligands with phosphorus and/or nitrogen as coordinating elements have been most extensively used.[2] Some of the recently developed nitrogen-based ligands deliver high enantioselectivities, but unsatisfactorily long reaction times are frequently required for full conversions.[3] In drug discovery and screening procedures, such as when using the principles of combinatorial chemistry, these long reaction times may cause costly delays in the development of lead compounds and new drugs.

Flash-heating by microwaves for acceleration of organic reactions is well established,[4] but it was only in the last few years that the power of the heating methodology was demonstrated in metal-catalysed coupling reactions, where the collapse of the catalytic system could be avoided by proper selection of conditions. The present applicant's own International patent application No. WO 97/00794 relates to such microwave induced organic reactions. Thus, selective Heck,[5] Suzuki,[6] and Stille[6] reactions, in solution or on solid phase, were accomplished in 1.5–12 min and in high yields with a variety of combinations of reactants.[5a,e,f,6]

Other examples of microwave-stimulated reactions, apart from those disclosed in the literature references cited herein, are given in the following patent publications.

Thus, U.S. Pat. No. 4,279,722 discloses the enhancement of the conversion of liquid hydrocarbons derived from petroleum in a catalytic petroleum refinery process by exposing a mixture of hydrocarbons and catalyst to microwave in the frequency range of about $2.5 \times 10^9$ to $10^{12}$ Hz.

U.S. Pat. No. 5,215,634 discloses a process for selectively converting methane and a hydrating agent to $C_3$ oxygenates. In particular, methane is reacted with water in the presence of a nickel metal powder catalyst using microwave irradiation to produce acetone and propanol.

U.S. Pat. No. 5,411,649 discloses selective production of ethane and ethylene in high yields by using particular catalysts and microwaves for controlled oxidation.

EP 0742189 A1 discloses production of an organo-nitrogen compound by irradiating a mixture of a catalyst, an organic compound and nitrogen with microwaves.

EP 0787526 A2 discloses the enhancement of catalytic reaction rates at low temperatures by utilising microwaves and other techniques, such as simulates boiling, ultrasonication, etc.

However, to the best of our knowledge, no reports have appeared on the impact of microwave irradiation on asymmetric transition metal catalysis in general, or on the reaction rate in such processes where allyl-metal complexes constitute a key intermediates in the catalytic cycle.

SUMMARY OF THE INVENTION

In view of the disadvantage of the known asymmetric allylic substitution reactions being so slow, the present inventors have developed a new method for performing asymmetric allylic substitution reactions. To the applicant's best knowledge, no previous reports have appeared on the impact of microwave irradiation on asymmetric transition metal catalysis in general and in particular not on reactions where allyl-metal-complexes constitute the key intermediate in the catalytic cycle.

The present invention provides a method of performing a transition metal-catalysed allylic substitution reaction, comprising the steps of:

a) preparing a reaction mixture comprising; (i) an allylic substrate which includes the structural element C=C—C—X, where X is a leaving group, (ii) a catalyst complex which includes a transition metal and one or more ligands, and (iii) a nucleophile; and b) exposing said reaction mixture to microwave energy from a controllable microwave source.

The present invention also provides a method for preparing a compound library of products of a transition metal-catalysed allylic substitution reaction, comprising the steps of:

a) preparing a reaction mixture comprising (i) n different species of allylic substrates which include the structural element C=C—C—X, where X is a leaving group, (ii) a catalyst complex which includes a transition metal and one or more ligands, and (iii) m different nucleophiles, wherein n is an integer in the range of 1–25 and m is an integer in the range of 1–10, with the proviso that the product n×m is at least 2, such as at least 3 or at least 4; and b) exposing said reaction mixture to microwave energy from a controllable microwave source.

In the steps a(ii) in the methods according to the invention, the catalyst complex can in certain cases preferably be generated by microwave-stimulated reaction between a catalyst precursor (precatalyst) and the free ligand.

Thus, it is also possible within the present invention to provide compound mixtures especially valuable for screening purposes.

The methods according to the present invention are particularly interesting where an asymmetric catalyst is utilised in that an enantiometic/diastereomeric excess of the desired product thereby can be obtained.

Figure 1:
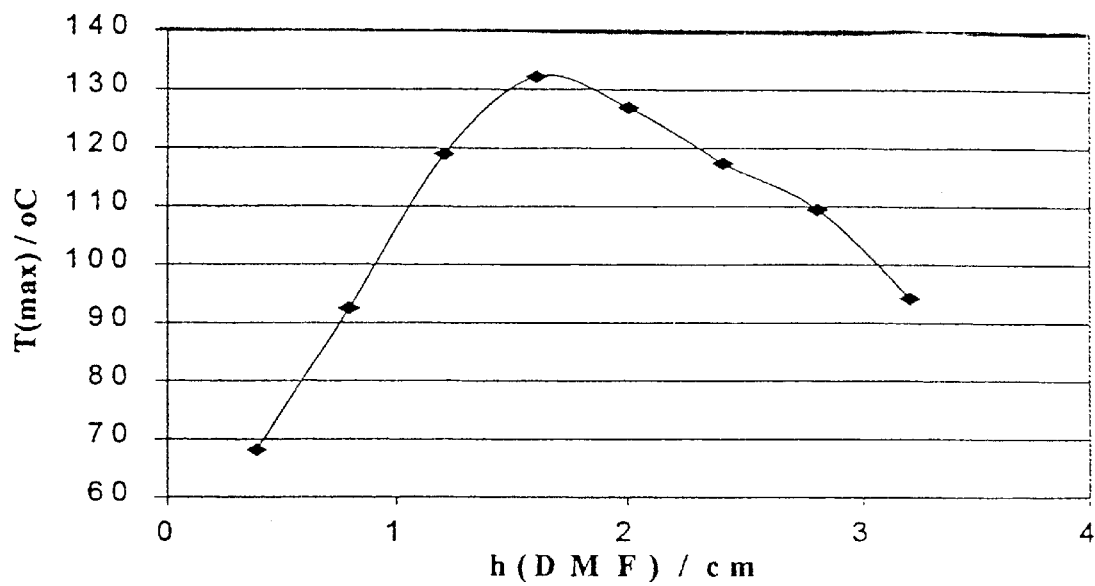
FIG. 1 illustrates the sample height dependence.

The present invention takes advantage of the benefits of microwave heating in allylic substitution reactions. In the present invention, the reaction mixture is preferably exposed to microwave energy in a single-mode microwave cavity.

The use of a single-mode microwave cavity allows the placement of the reaction tube at a fixed position of more uniform and more intense microwave irradiation than can be obtained in a multimode reactor.[7] Examples of suitable microwave facilities are commercial ovens and cavities where a magnetron is used as a microwave source. The Microwell™ products from Labwell, Sweden are especially suitable for the present invention. However, it is envisaged that especially interesting alternatives are semiconductor microwave generators which may have a particular value concerning the compound library (combinatorial chemistry) applications within the present invention.

With respect to the frequency and power, the microwave energy applied according to the present invention typically has a frequency in the range of 300 MHz to 300 GHz, preferably in the range of 900 MHz to 23 GHz, in particular in the range of 1.5 GHz to 10.0 GHz and is typically supplied to the reaction mixture at a power of 1–1000 W, preferably 10–1000 W, in particular 20–500 W. In contrast to conventional heating where reaction times are in the range of hours or days, the microwave energy is typically supplied to the reaction mixture for a period of 1 s–1 h, preferably 6 s–30 min, in particular 15 s–15 min. Depending on the microwave source, its frequency and power, as well as the reaction components, exposure to microwave energy for less than one second may be sufficient to facilitate the reaction.

Microwave energy facilitates the reaction and heats the reaction system. In certain embodiments of the substitution reaction, conditions may be such that the reaction is run at low temperatures, such as below room temperature and as low as −45° C. The microwave energy in itself may provide the necessary energy input into the system to facilitate the reaction. The energy may be dissipated as heat yet may not be necessarily detectable or will be limited to a microenvironment within the reaction system.

The catalysts used within the present invention are transition metal catalysts which together with one or more ligands form a catalyst complex. The transition metal of the catalyst complex is typically selected from cobalt (Co), copper (Cu), iridium (Ir), iron (Fe), manganese (Mn), molybdenum (Mo), nickel (Ni), osmium (Os), palladium (Pd), platinum (Pt), rhenium (Re), rhodium (Rh), ruthenium (Ru) or tungsten (W), preferably Ir, Mo, Ni, Os, Pd, Pt, Ru, Rh and W, in particular Mo and Pd.

As mentioned above, the transition metal forms a complex with one or more ligands. The ligands coordinates with the transition metal through one or more coordinating atoms. In order to exploit the full scope of the present invention, namely to prepare compounds in enantiomeric/diasteromeric excess in an allylic substitution reaction, the ligand(s) of the catalyst complex is/are preferably selected from asymmetric ligands such as $C_1$- or $C_2$-symmetrical ligands.

Irrespective whether the ligands are symmetric or asymmetric, the ligand(s) of the catalyst complex typically has/have coordinating atoms selected from the groups consisting of antimony (Sb), arsenic (As), carbon (C) (especially relevant where the ligand is carbonmonooxide or where a carbanion is used as a ligand), nitrogen (N), oxygen (O), phosphorus (P), selenium (Se), sulphur (S) and/or tellurium (Te), preferably As, N, O, P, Se and S, in particular N and P.

In an embodiment of the present invention, the ligand(s) of the catalyst complex is/are monodentate ligands, preferably monodentate ligands with phosphorus or nitrogen. Asymmetric examples of such ligands are

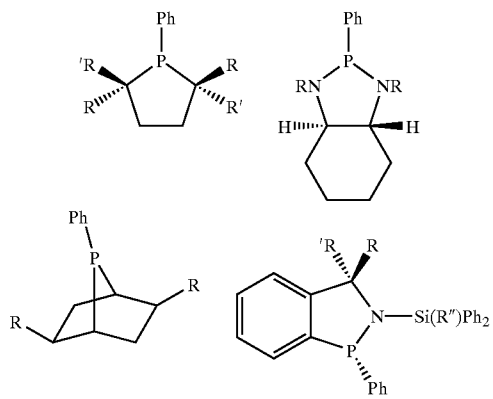

wherein Ph designates phenyl, R and R' each independently is selected from hydrogen, $C_{1-10}$-alkyl and phenyl, and R" is selected from $C_{1-10}$-alkyl and phenyl. Particular examples are

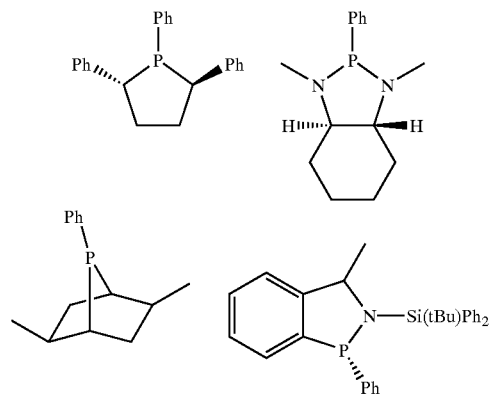

In another embodiment of the present invention, the ligand(s) of the catalyst complex is/are bidentate ligands, preferably bidentate ligands with phosphorus and/or nitrogen.

Examples of asymmetric bidentate ligands with nitrogen are

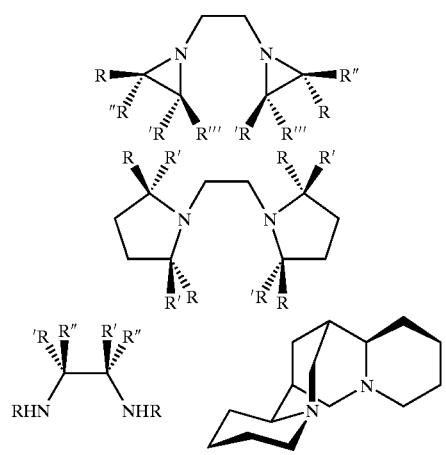

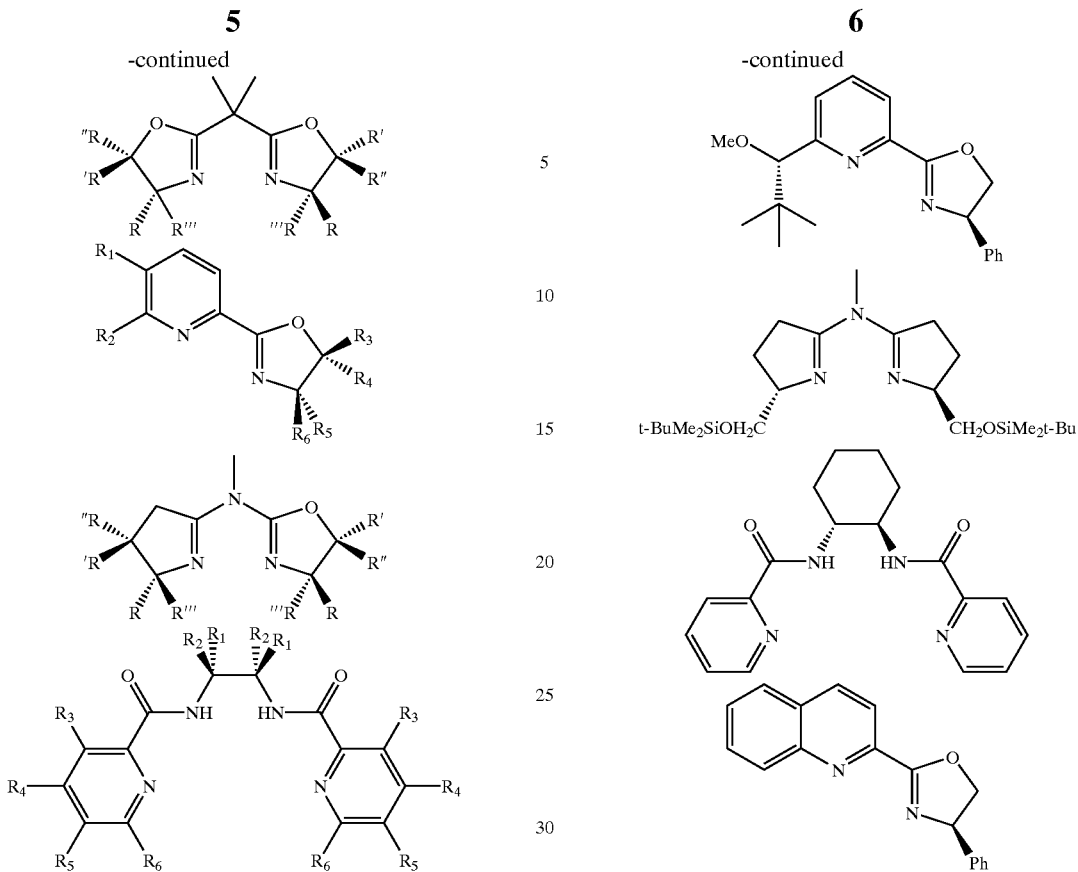

wherein $R_1$, $R_2$, $R_3$, $R_4$, $R_5$, and $R_6$ each independently is selected from hydrogen, $C_{1-10}$-alkyl, aryl, heteroaryl, hydroxy, alkoxy, di($C_{1-10}$-alkyl)amino, ($C_{1-10}$-alkyl)thio, and tri($C_{1-10}$-alkyl and/or phenyl)silyl, where different R may interconnect to form for example a benzene ring.

Particular examples are

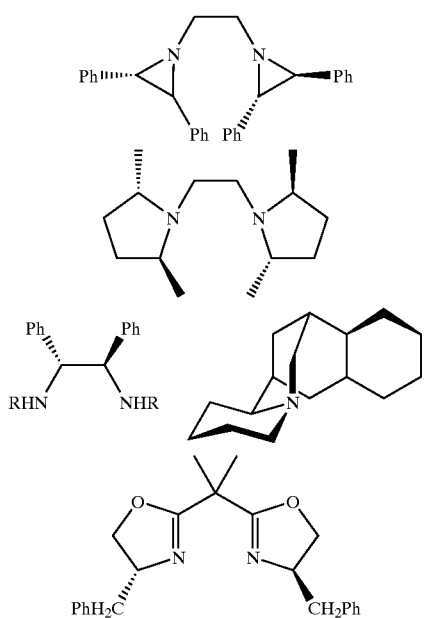

The above mentioned ligands are in our particular case thought to occupy two coordination sites on the metal. It can however be recognised that many will coordinate as multidentate ligands, e.g. three- or even tetradentate ligands, depending on choice of reaction parameters, for example metal or solvent.

Examples of asymmetric bidentate ligands with phosphorus are

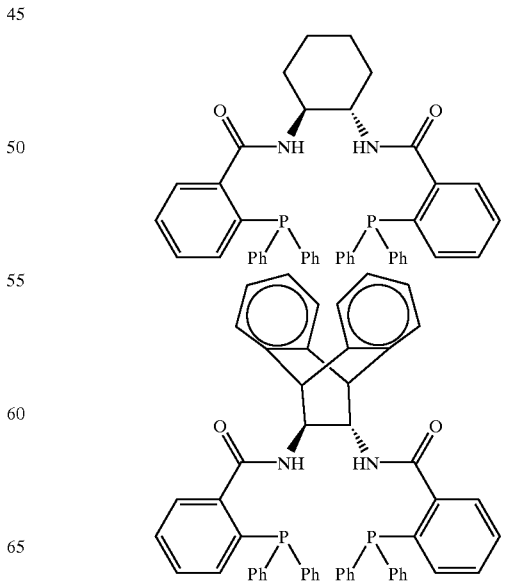

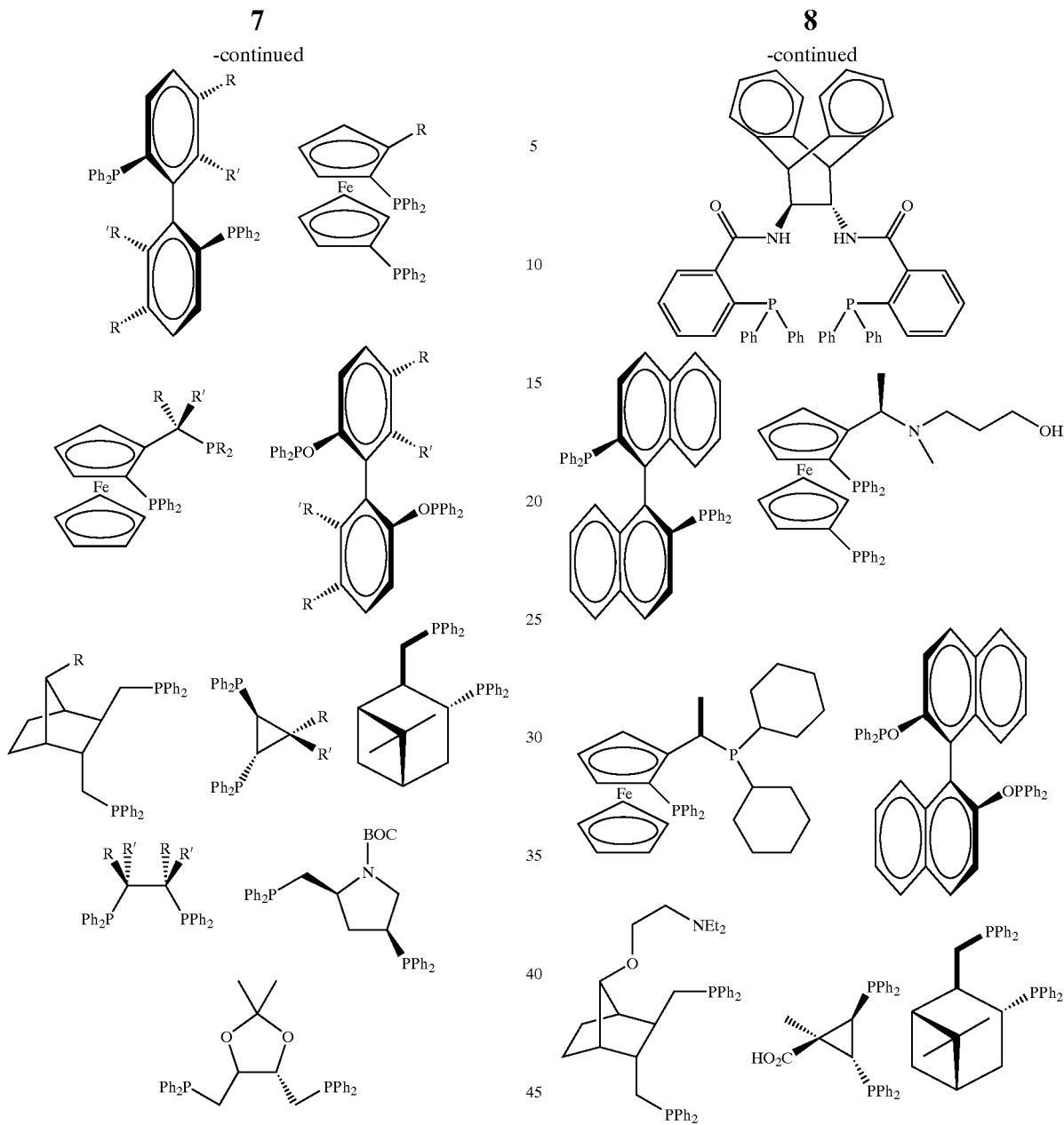

wherein Ph designates phenyl, and R and R' each independently is selected from hydrogen, $C_{1-10}$-alkyl, and phenyl, where R and R' together with the interconnecting atoms may form a carbocyclic ring such as a benzene ring.

Particular examples are (+)-BINAP and (−)-BINAP (2,2'-Bis(diphenylphosphino)-1,1'-binaphthyl), (R)-(+)-2,2'-bis(di-p-tolylphosphino)-1,1'-binaphthyl,

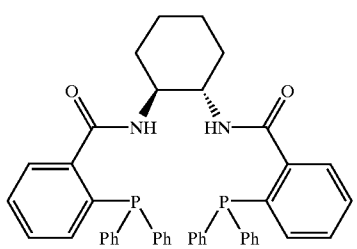

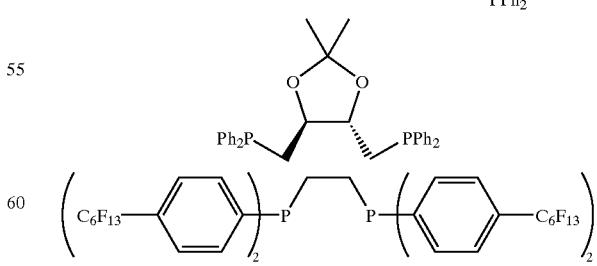

Examples of asymmetric bidentate ligands with phosphorus/nitrogen are

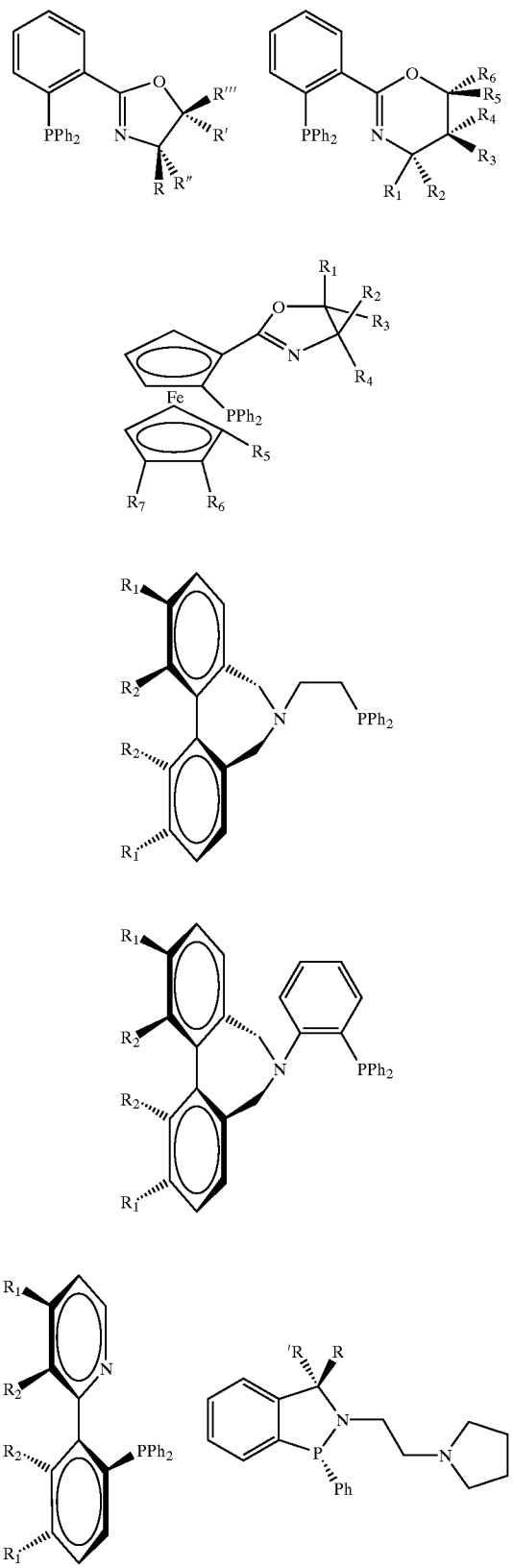
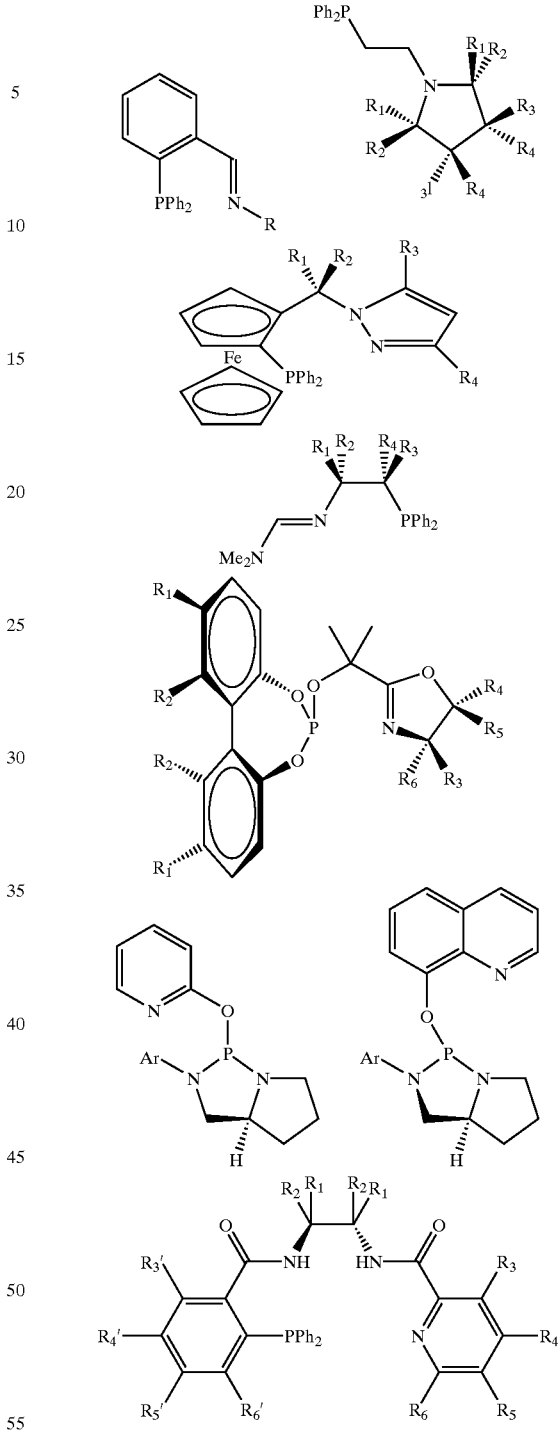

wherein Ph designates phenyl, Ar designates aryl or heteroaryl, R and R' each independently is selected from hydrogen, $C_{1-10}$-alkyl and phenyl, and $R_1$, $R_2$, $R_3$, $R_4$, $R_5$, $R_{-6}$, $R_3'$, $R_4'$, $R_5'$, $R_6'$ and $R_7$ each independently is selected from hydrogen, $C_{1-10}$-alkyl and phenyl, where $R^1$ and $R^2$ together with the interconnecting atoms may form a carbocyclic ring such as a benzene ring. Specific examples are (−)-(S)-4-iso-propyl-2-(2-(diphenylphosphino)phenyl)-4,5-dihydrooxazole, (−)-(S)-4-tert-butyl-2-(2-(diphenylphosphino)phenyl)-4,5-dihydrooxazole, (+)-(R)-4-phenyl-2-(2-(diphenyl-phosphino)phenyl)-4,5-dihydrooxazole,

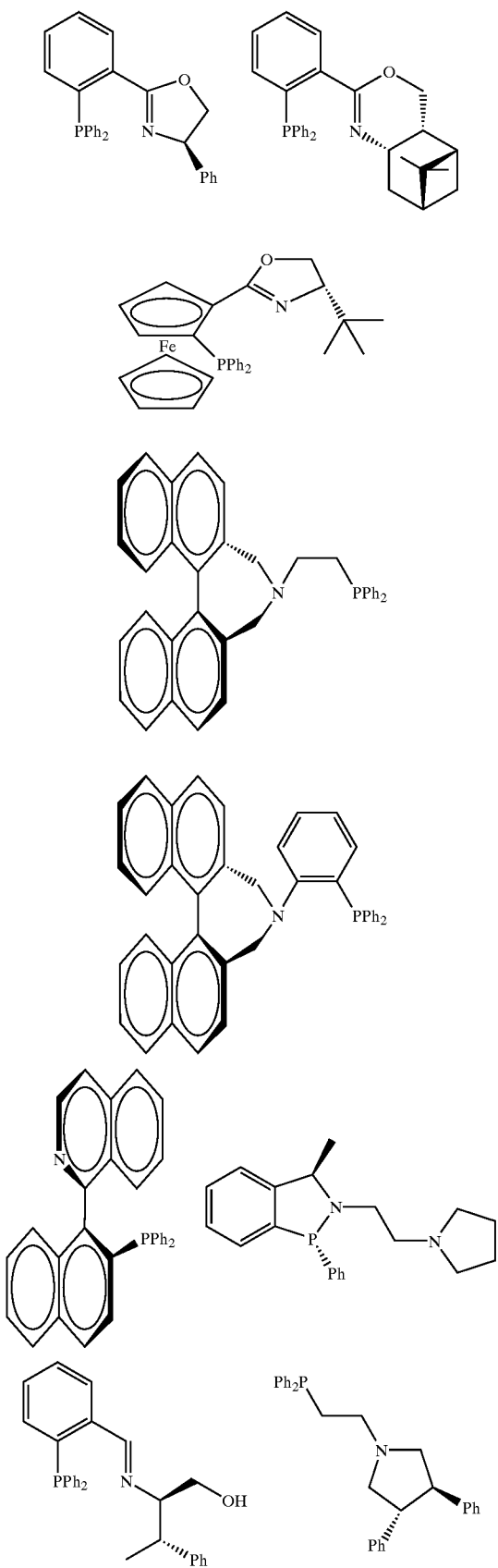

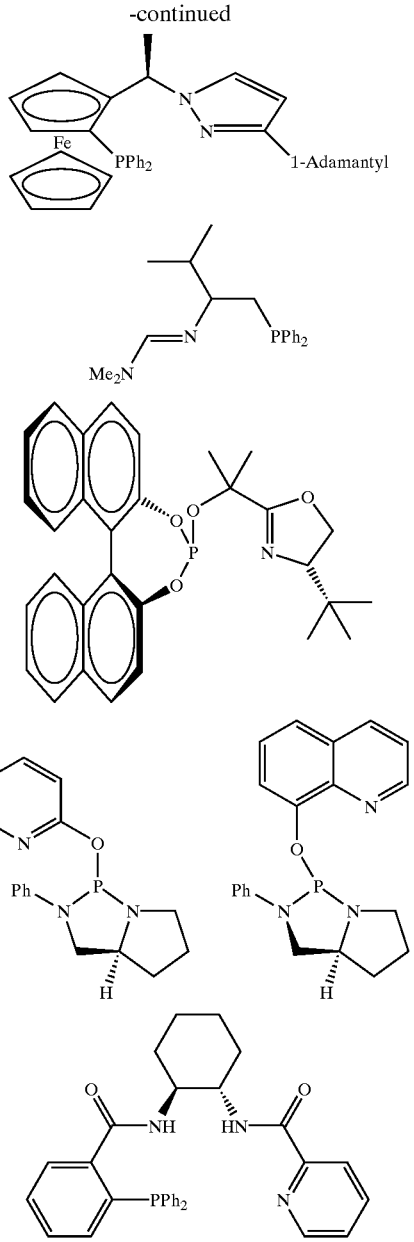

The above mentioned ligands are in our particular case thought to occupy two coordination sites on the metal. It can however be recognised that many will coordinate as multidentate ligands, e.g. three- or even tetradentate ligands, depending on choice of reaction parameters, for example metal or solvent.

In still another embodiment of the present invention, the ligand(s) of the catalyst complex is/are multidentate ligands which comprise(s) 3–6 coordinating atoms, preferably multidentate ligands with phosphorus and/or nitrogen.

In one embodiment, the catalyst complex comprises one ligand. In another embodiment, the catalyst complex comprises more than one ligand, preferably two ligands. Typically catalyst complexes with palladium are bidentate at Pd coordinating two monodentate or one bidentate ligand.

The specific ligands mentioned above are particularly interesting in a catalyst complex for allylic substitutions where the transition metal is typically selected from Co, Cu, Ir, Fe, Mn, Mo, Ni, Os, Pd, Pt, Re; Rh, Ru or W, preferably Mo, Ni, Os, Pd, Pt, Ru and W, in particular Mo and Pd.

One embodiment of the present invention which is considered to be particularly interesting is where the transition metal molybdenum complexes with one or more ligand(s) of the type

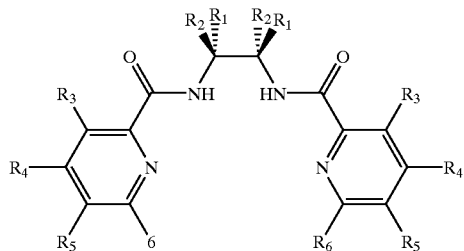

wherein $R_1$, $R_2$, $R_3$, $R_4$, $R_5$, and $R_{-6}$ each independently is selected from hydrogen, $C_{1-6}$-alkyl, aryl, heteroaryl, hydroxy, alkoxy, di($C_{1-6}$-alkyl)amino, $C_{1-6}$-alkylthio, and tri($C_{1-6}$-alkyl and/or phenyl)silyl, where two of $R_1$ and $R_2$ together with the interconnecting atoms may form a carbocyclic ring.

The catalyst complex may be prepared (or otherwise acquired) prior to the reaction, or the catalyst complex may be formed in situ. In small reaction series it is convenient to prepare the catalyst in situ. On more extensive use, a pre-formed catalyst would often be preferred. In an illustrative example where the catalyst comprises palladium, the catalyst is formed by dissolving the ligand and palladium compound (conveniently (Pd($\eta^3$-$C_3H_5$)$\mu$-Cl)$_2$) and allowing the components to react for a period of time depending on the ligand. With a typical N,N-ligand or a typical P,N-ligand the solution is often stirred at around 50° C., e.g. for 2 h. With a typical P,P-ligand stirring for about 30 min at room temperature is often sufficient. The catalyst could very well be isolated by evaporation of the solvent, but preferably a silver salt with a non-coordinating counterion ($BF_4^-$, $PF_6^-$, $TfO^-$, etc) is added. AgCl is removed by filtration, and the catalyst is precipitated. Thus preferably, the catalyst is obtained in the form of a metal complex with a non-coordinating counterion. With N,N-ligands the catalyst is most stable in Pd(II)-form and thus the salt is preferred. But it is also possible to isolate the catalyst in Pd(0)-form as a Ligand-Pd-Solvent complex, even though this often is more difficult and the catalyst will be more sensitive. The same applies to a lesser extent to P,P-ligands, however, in some cases stable Ligand-Pd(0) complexes can be isolated, e.g. Pd(PPh$_3$)$_4$ or Pd(DPPE)$_2$, where DPPE is 1,2-bis(diphenylphosphino)ethane.

In another example, where the catalyst comprises molybdenum, the molybdenum precursor (conveniently Mo(CO)$_6$) is simply mixed with the ligand and the mixture is heated in a microwave cavity for some minutes, e.g. 1–5 min. The active catalyst can be used directly without any further manipulation or purification.

The allylic substrate to be used within the present inventions comprises the structural element C=C—C—X. More specifically, the allylic substrate can be illustrated with general formula CD

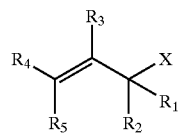

wherein $R_1$, $R_2$, $R_3$, $R_4$ and $R_5$ independently are selected from hydrogen, optionally substituted $C_{1-12}$-alkyl, optionally substituted aryl, optionally substituted heteroaryl, optionally substituted $C_{1-12}$-alkoxy, optionally substituted aryloxy, optionally substituted heteroaryloxy, tri($C_{1-10}$-alkyl and/or phenyl)silyl, or two of the substituents $R_1$, $R_2$, $R_3$, $R_4$ and $R_5$ together form a carbocyclic ring; and where X is a leaving group, and where X together with $R_1$ and the interconnecting atom may form an epoxide or an aziridine.

In cases where X together with $R_1$ and the interconnecting atom form an epoxide or an aziridine, these may be in racemic or non-racemic mixtures, or as enatiomerically or diasteromerically pure or enriched forms.

In the case where two of the substituents $R_1$, $R_2$, $R_3$, $R_4$ and $R_5$ together form a carbocyclic ring, such a ring is typically a carbocyclic ring comprising 4–8 carbon atoms. The ring may be fully or partially saturated, but it is preferably fully saturated. The ring may carry one or more substituents of the same kind as those defined for $R_1$—$R_5$.

In the case where X together with $R_1$ and the interconnection atom form an epoxide or an aziridine, $R_1$ designates $C_{1-12}$-alkylene, e.g. methylene or ethylene, and X designates O or N, where the α-carbon of the $C_{1-12}$-alkylene is linked to the O or N and the interconnecting atom, respectively.

It should be understood that the above formula is in no way restrictive for the present invention, as the present invention provides a method where almost any substrate of the allylic type can be used, i.e. the substituents $R_1$—$R_5$ should simply be selected with due regard to the functional groups involved. As will be known to the person skilled in the art, the substrate should be selected so that any functional groups or entities of the substrate (except for the allylic system) should be substantially unaffected by the reactions conditions. Preferably, any reactive groups are, where desirable or necessary, protected or masked in order to ensure that the substitution reaction is regioselective (and, if desirable, or necessary: stereoselective). Protection groups are known to the person skilled in the art, see e.g. those described by Greene, T. W. and Wuts, P. G. M. (Protecting Groups in Organic Synthesis).

Preferred "leaving groups" are selected from bromo, chloro, iodo, —OC(=O)R (such as acetoxy), —OCO$_2$R, —OC(=S)R, —SC(=O)R, —SC(=S)R —OPO(OR)$_2$, —OSOR, —OSO$_2$R, —OR, —OR$_2^+$, —SR$_2^+$, —SO$_2$R, —NR$_3^+$, —PR$_3^+$, —NO$_2$, —CN, wherein R is selected from hydrogen, $C_{1-10}$-alkyl, aryl, and heteroaryl, among which acetoxy (—OAc), methyl/ethyl/benzyl/tert-butyl carbonate (—OCO$_2$Me, —OCO$_2$Et, —OCO$_2$Bn, —OCO$_2^t$Bu) especially preferred.

Embodiments wherein the "leaving group" is of the family of —Y$^1$—C(=Y$^2$)Y$^3$—R, where Y$^1$—Y$^3$ can be independently selected from the group comprising of oxygen, nitrogen, and sulfur and R is as defined above are particularly interesting. The tautomeric forms of the family of leaving groups Y—C(=Y)Y—R, where Y=O, N, or S, are also preferred leaving groups. Some examples of the family of leaving groups Y—C(=Y)Y—R include carbonates, thiocarbonates, carbamates and thiocarbamates.

Also preferred are substrates where at least one of $R_1$ to $R_5$ is aryl such as phenyl.

Some illustrative examples of substrates are

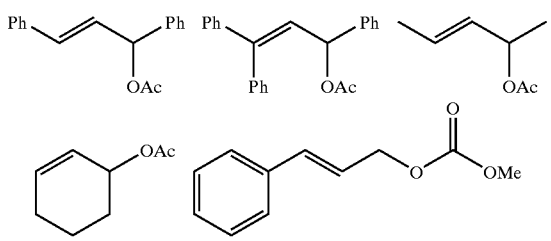

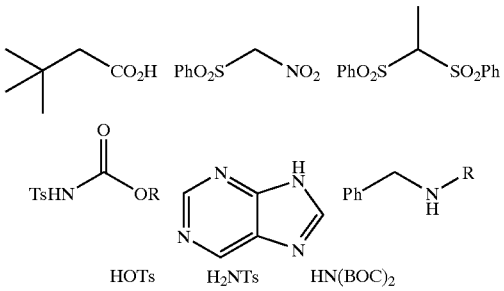

where Ph designates phenyl, and R is as defined above. It should be understood that the above-mentioned examples represent the protonated forms of the nucleophiles, which are deprotonated prior to use.

For some of the nitrogen, sulfur or oxygen nucleophiles, deprotonation is however not always necessary as will be clear for the person skilled in the art.

In some cases, a mild base will be sufficient to deprotonate the nucleophile precursor. Mild bases have a $pK_a$ above 7.

Nucleophiles may also be generated in situ by reacting a nucleophile precursor with a strong base, such as a strong base having a $pK_a$ in the range of 10–50. Alternatively, the nucleophile may be pre-prepared as is shown in the examples with sodium dimethylmalonate.

In order to enhance the nucleophilicity of the nucleophile, the strong base is used in combination with a crown ether, a quarternary ammonium salt, or quaternary phosphonium salts.

The methods according to the present invention are typically performed in solution, i.e. the substrate, the catalyst complex and the nucleophile are mixed in a solvent. When a solvent is used, it is preferred that the dissipation factor (or loss tangent) is greater than about 0.04 at rt. Examples of suitable solvents are acetonitrile, DMF, DMSO, NMP, water, MeOH, EtOH, benzonitrile, ethylene glycol, acetone, THF, $CH_2Cl_2$, $CHCl_3$, among which acetonitrile and THF are preferred.

The relative ratio between the substrate, the complex catalyst and the nucleophile and the concentration of these constituents in any solvent are determined with due regard to the reactivity of the nucleophile and substrate, and with regard to economical considerations. As a general guideline, the concentration of the allylic substrate in the solvent is typically in the range of $1*10^{-3}$–10 M, preferably 0.05–2 M, in particular 0.3–1 M; the concentration of the nucleophile in the solvent is typically in the range of $1*10^{-3}$–10 M, preferably 0.05–2 M, in particular 0.15–1 M; and the concentration of the catalyst complex in the solvent is typically in the range of $1*10^{-9}$–1 M, preferably $1*10^{-6}$–0.1 M, in particular $5*10^{-3}$–0.01 M.

The method according to the present invention may also be conducted where the reaction mixture does not comprise a solvent ("neat" reaction).

In the case where a solvent is used as well as in the case where the reaction is performed "neat", the molar ratio between the nucleophile and the allylic substrate is typically in the range of 1000:1–1:1000, preferably 10:1–1:10, in particular 3:1–1:3; and the molar ratio between the catalyst complex and the allylic substrate typically is typically in the range of 1:1–1:1*10$^9$, preferably 1:10–1:1*10$^4$, in particular 1:20–1:60. As mentioned above, the ratios are chosen with due respect to the cost of the individual constituents.

One of the advantages of the methods of the present invention is the possibility of conducting the reaction in a

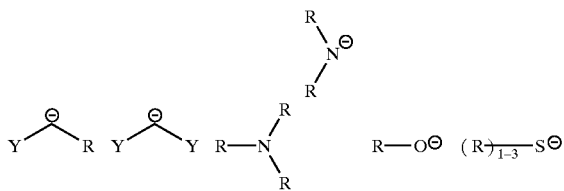

wherein Y is an electron withdrawing group and each R independently is selected from hydrogen, $C_{1-12}$-alkyl, aryl, aryl-$C_{1-10}$-alkyl (e.g. benzyl), alkylheteroaryl, trin($C_{1-12}$-alkyl and/or phenyl)silyl, di($C_{1-12}$-alkyl)amino, $C_{1-12}$-alkoxy, aryloxy, $C_{1-12}$-alkylsulphonyl, and $C_{1-12}$-alkyloxycarbonyl.

Useful specific examples are

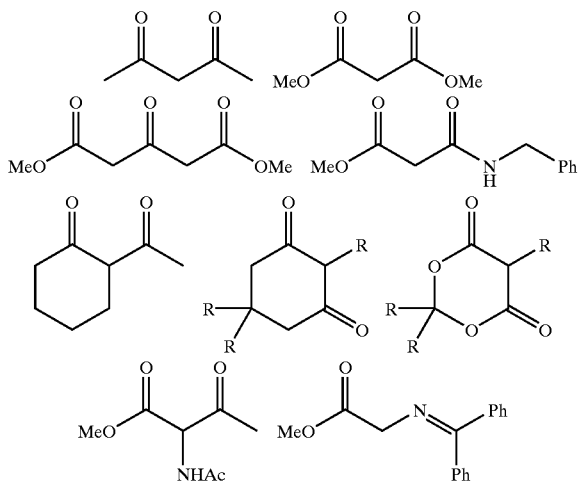

stereoselective manner. Stereoselectivity is obtained where the catalyst complex comprises one or more asymmetrical ligands. Thus, in particular, the allylic substitution reaction yields a enantiomeric excess (ee) of one of the theoretically possible reaction products. The enantiomeric excess (ee) is typically >60%, preferably >70%, more preferably >80%, in particular >90%, such as >95%. For certain substrates the allylic substitution reaction yields a diastereomeric excess (de) of one of the theoretically possible reaction products. The diasteromeric excess (de) is typically >60%, preferably >70%, more preferably >80%, in particular >90%, such as >95%.

The present invention has special interest in the preparation (either directly or via intermediates) of a number of interesting biologically active compounds, e.g. carbonucleosides such as aristeromycin and carbovir, alkaloids such as (+)-gamma-lycorane and pancratistatin, and antifungal agents such as polyoxins and nikkomycins, and intermediates therefore, e.g. allylic sulfones.

An interesting field of application is the synthesis of compounds having a radioactive nuclide with very short half-life incorporated in the structure. Such compounds are, e.g., used in the so-called PET-techniques (Positron Emission Tomography). The radioactive nuclide may arise from either the allylic substrate or the nucleophile. Thus, in an interesting embodiment of the present invention, the allylic substrate and/or the nucleophile have been enriched with a radio-isotope. In particular, the radio-isotope is a positron emitting isotope.

Another particularly interesting application of the fast and robust methods of the present invention is the preparation of compound libraries, which may be especially suitable for the production of compound libraries. Easy access to such compound libraries gives an excellent opportunity for screening a large number of interesting drug candidates in drug discovery.

Thus, as mentioned above, the present invention also provides a method for preparing a compound library of products of a transition metal-catalysed allylic substitution reaction, comprising the steps of:

a) preparing a reaction mixture comprising (i) n different species of allylic substrates which include the structural element C=C—C—X, where X is a leaving group, (ii) a catalyst complex which includes a transition metal and one or more ligands, and (iii) m different nucleophiles, wherein n is an integer in the range of 1–25 (such as 1–10 or 2–8) and m is an integer in the range of 1–10 (such as 1–5 or 2–5), with the proviso that the product n×m is at least 2, such as at least 3 or at least 4; and b) exposing said reaction mixture to microwave energy from a controllable microwave source.

In step a(ii), the catalyst complex, can in certain cases preferably be generated by microwave-stimulated reaction between a catalyst precursor (precatalyst) and the free ligand.

It should be noted that the specific embodiments and variant with respect to conditions, substrates and catalysts mentioned above also apply for the method for preparation of compound libraries (compound library of products of a transition metal-catalysed allylic substitution reaction) are as defined above for the general method.

With respect to the microwave source, it is envisaged that semiconductor microwave systems might be especially applicable.

In view of the excellent stereoselectivity obtained with the methods of the present invention, a further aspect relates to the use of a transition metal-catalyst complex including a $C_1$- or $C_2$-symmetrical ligand as defined herein in a microwave promoted allylic substitution reaction.

Definitions

In the present context, the term "$C_{1-12}$-alkyl" is intended to mean a linear, cyclic or branched hydrocarbon group having 1 to 12 carbon atoms, such as methyl, ethyl, propyl, iso-propyl, cyclopropyl, butyl, tert-butyl, iso-butyl, cyclobutyl, pentyl, cyclopentyl, hexyl, cyclohexyl, heptyl, cyclohexylmethyl, octyl, nonyl. Analogously, the term "$C_{1-10}$-alkyl" is intended to mean a linear, cyclic or branched hydrocarbon group having 1 to 10 carbon atoms, such as methyl, ethyl, propyl, iso-propyl, pentyl, cyclopentyl, hexyl, cyclohexyl, heptyl, cyclohexylmethyl, octyl, nonyl, and the term "$C_{1-4}$-alkyl" is intended to cover linear, cyclic or branched hydrocarbon groups having 1 to 4 carbon atoms, e.g. methyl, ethyl, propyl, iso-propyl, cyclopropyl, butyl, iso-butyl, tert-butyl, cyclobutyl. Preferred examples of "$C_{1-10}$-alkyl" are methyl, ethyl, propyl, iso-propyl, butyl, tert-butyl, iso-butyl, pentyl, cyclopentyl, hexyl, cyclohexyl, in particular methyl, ethyl, propyl, isopropyl, tert-butyl, iso-butyl and cyclohexyl.

In addition to the above unsubstituted alkyl group, the term "alkyl" is also intended to cover any and all of the fluorinated analogues thereof. Fluorinated analogues are intended to include poly-fluorinated analogues and per-fluorinated analogues alike. Poly-fluorinated analogues are compounds with high fluorine content whereas per-fluorinated analogues are fully substituted with fluorine. Examples of poly-fluorinated analogues are pentafluoroethane ($C_2$), heptafluoro propane ($C_3$), etc. Thus in the following, irrespective whether "alkyl" is referred to as a radical or as a substituent, the term should also encompass the fluorinated analogues. In one possible embodiment, essentially all alkyl groups are poly-fluorinated. In another possible embodiment, none of the alkyl groups are poly-fluorinated, but may—if so indicated—be substituted as mentioned below. Typically, the fluorinated alkyl can be linked through a non-fluorinated linker such as an olefin, e.g. $CH_2=CH_2-C_6F_{13}$.

In the present context, i.e. in connection with the term "alkyl", the term "optionally substituted" is intended to mean that the group in question may be substituted one or several times, preferably 1–3 times, with group(s) selected from hydroxy (which when bound to an unsaturated carbon atom may be present in the tautomeric keto form), $C_{1-10}$-alkoxy (i.e. $C_{1-10}$-alkyl-oxy), carboxy, oxo (forming a keto or aldehyde functionality), $C_{1-10}$-alkoxycarbonyl, $C_{1-10}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-10}$-alkyl)amino, carbamoyl, mono- and di($C_{1-10}$-alkyl)aminocarbonyl, amino-$C_{1-10}$-alkyl-aminocarbonyl, mono- and di($Cl_{1-10}$-alkyl)amino-$C_{1-10}$-alkyl-aminocarbonyl, $C_{1-10}$-alkyl-carbonylamino, cyano, guanidino, carbamido, $C_{1-10}$-alkanoyloxy, sulphono, $C_{1-10}$-alkylsulphonyloxy, arylsulphonyloxy, trihalomethylsulphonyloxy, nitro, sulphanyl, $C_{1-10}$-alkylthio and halogen, where any aryl and heteroaryl may be substituted as specifically describe below for "optionally substituted aryl and heteroaryl".

Preferably, the substituents are selected from hydroxy, $C_{1-10}$-alkoxy, carboxy, $C_{1-10}$-alkoxycarbonyl, $C_{1-10}$-alkyl carbonyl, formyl, aryl, aryloxycarbonyl, arylcarbonyl, heteroaryl, amino, mono- and di($C_{1-10}$-alkyl)amino, carbamoyl, mono- and di($C_{1-10}$-alkyl)-aminocarbonyl, amino-$C_{1-10}$-alkyl-aminocarbonyl, mono- and di($C_{1-10}$-alkyl)amino-$C_{1-10}$-alkyl-aminocarbonyl, $C_{1-10}$-alkylcarbonylamino, cyano, carbamido, halogen, where aryl and heteroaryl may be substituted 1–5 times, preferably 1–3 times, with $C_{1-10}$-alkyl, $C_{1-10}$-alkoxy, nitro, cyano, and amino. Especially preferred examples are hydroxy, $C_{1-10}$-alkoxy, carboxy, aryl, heteroaryl, amino, mono- and di($C_{1-10}$-alkyl)amino, and halogen, where aryl and heteroaryl may be substituted 1–3 times with $C_{1-10}$-alkyl, $C,O_{10}$-alkoxy, nitro, cyano, amino or halogen. "Halogen" includes fluoro, chloro, broto and iodo.

In the present context the term "aryl" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl, cyclopentadienyl anion and xanthenyl, among which phenyl is a preferred example.

The term "heteroaryl" is intended to mean a fully or partially aromatic carbocyclic ring or ring system where one or more of the carbon atoms have been replaced with heteroatoms, e.g. nitrogen (=N— or —NH), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl and phenoxazonyl.

In the present context, i.e. in connection with the terms "aryl" and "heteroaryl", the term "optionally substituted" is intended to mean that the group in question may be substituted one or several times, preferably 1–5 times, in particular 1–3 times, with group(s) selected from hydroxy (which when present in an enol system may be represented in the tautomeric keto form), $C_{1-10}$-alkyl, $C_{1-10}$-alkoxy, oxo (which may be represented in the tautomeric enol form), carboxy, $C_{1-10}$-alkoxycarbonyl, $C_{1-10}$-alkylcarbonyl, formyl, aryl, aryl-oxy, aryloxycarbonyl, arylcarbonyl, heteroaryl, amino, mono- and di($C_{1-10}$-alkyl)amino; carbamoyl, mono- and di($C_{1-10}$-alkyl)aminocarbonyl, amino-$C_{1-10}$-alkyl-aminocarbonyl, mono- and di($C_{1-10}$-alkyl)amino-$C_{1-6}$-alkyl-aminocarbonyl, $C_{1-10}$-alkylcarbonylamino, cyano, guanidino, carbamido, $C_{1-10}$-alkanoyloxy, sulphono, $C_{1-10}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1–3 times with $C_{1-4}$-alkyl, $C_{1-4}$-alkoxy, nitro, cyano, amino or halogen. Preferred examples of substituents are hydroxy, $C_{1-10}$-alkyl, $C_{1-10}$-alkoxy, carboxy, $C_{1-10}$-alkoxycarbonyl, $C_{1-10}$-alkylcarbonyl, aryl, amino, and mono- and di($C_{1-10}$-alkyl)amino, wherein aryl may be substituted 1–3 times with $C_{1-10}$-alkyl, $C_{1-10}$-alkoxy, nitro, cyano, amino or halogen.

The term "alkoxy" means "alkyl-oxy", the term "aryloxy" means "aryl-oxy" (aryl—O—), and "heteroaryloxy" means "heteroaryl-oxy".

In the present context, the term "carbocyclic ring" is intended to mean a non-aromatic or fully or partially aromatic carbocyclic ring or ring system. Examples of such rings are benzene, naphthalene, 1,2,3,4-tetrahydronaphthalene, cyclobutane, cyclopropane, cyclohexane, cycloheptane, and cyclooctane.

In the present context, the term "tri($C_{1-10}$-alkyl and/or phenyl)silyl" is intended to mean a silyl group substituted three times with groups selected from $C_{1-10}$-alkyl and phenyl, i.e. the silyl group is substituted p times with a $C_{1-10}$-alkyl group and q times with a phenyl group, where p+q is 3. Examples are triphenylsilyl, tert-butyl-diphenyl-silyl, etc.

In the present context, the term "electron withdrawing group" is intended to have is normal meaning (see, e.g., March, J., Advanced Organic Chemistry, Reactions, Mechanisms, and Structure., $3^{rd}$ ed., 1985, John Wiley, New York, especially pp 16–18.) Illustrative examples are carbonyl groups including $C_{1-12}$-alkylcarbonyl, $C_{1-12}$-alkoxycarbonyl, arylcarbonyl, aryloxycarbonyl, mono- or di($C_{1-12}$-alkyl)aminocarbonyl, $C_{1-12}$-alkylsulphonyl, arylsulphonyl, and derivative (e.g. substituted variants) thereof.

The Method and Illustrative Results

In the following, the examples shown in the experimental section are discussed.

Palladium

Racemic (E)-1,3-diphenyl-2-propenyl acetate (1), .which is a commonly used substrate in asymmetric palladium-catalysed allylic alkylations, reacts smoothly with dimethyl malonate in catalytic systems where phosphine ligands are employed, while very long reaction times sometimes are needed with bidentate nitrogen ligands.[2,3] The transformation of 1 into 2 (see FIG. 1) was therefore chosen as a suitable model reaction for studies of microwave flash-heating. Three classes of ligands with diverse inherent properties were assessed. One of them, (+)-BINAP (2,2'-bis (diphenyl-phosphino)-1,1'-binaphthyl) (4), constitutes an example of an often used $C_2$-symmetric bis-phosphine ligand.[8] As examples of N,N- and P,N-ligands, $C_1$-symmetric (4'R)-2-(4',5'-dihydro-4'-phenyl-2'-oxazolyl) quinoline (3)[9] and three different phosphineoxazolines (7, 13, 14)[10] were chosen.

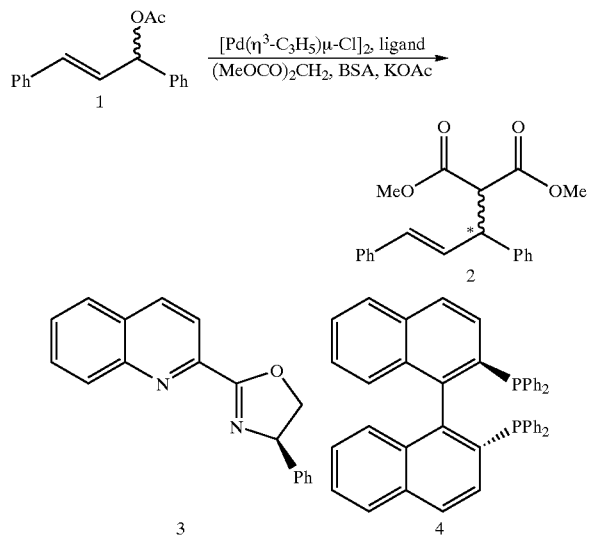

-continued 7 (PPh₂, oxazoline with iPr)

13 (PPh₂, oxazoline with tBu)

14 (PPh₂, oxazoline with Ph)

The alkylations were conducted essentially following the procedure by Trost et al[11] using N, O-bis(trimethylsilyl) acetamide (BSA) as base, with modifications by Leuteneg-ger et al[12a] for the nitrogen ligands and by Brown et al[12b] for BINAP. A π-allylpalladium(ll)-ligand complex was prepared in situ and a low concentration of the nucleophile was generated from dimethyl malonate in the presence of BSA and a catalytic amount of KOAc. The microwave heating was performed with a single-mode cavity in sealed heavy-walled Pyrex tubes.[13] (One often overlooked hazard that may become prevalent under microwave irradiation is the formation of electrical arcs. Arcing could result in vessel rupture if air and flammable compounds are involved. We believe the possibility to run reactions in an inert gas atmosphere is a distinct advantage with the sealed reaction vessel strategy (as compared to running the reactions in an open reaction vessel). The experiments were conducted in acetonitrile which is known to possess a sufficiently high dissipation factor (tan δ(rt)=0.050)[4] to be efficiently heated under microwave irradiation.[4,14] The results are summarised in Table 1.

In Table 1, the microwave experiments with selected combinations of irradiation time and power that resulted in complete consumption of the starting material are summarised. The examples in Table 1 disclose that with an appropriate choice of microwave power and irradiation time complete conversion and high yields can be obtained in very short reaction times. The reaction with ligand 4 delivered a slightly higher enantiomeric excess and was considerably faster than the reactions with 3 as ligand, which is in agreement with non-microwave mediated reactions in dichloromethane.[9,12a] Neither of them induced extreme enantioselectivities in acetonitrile. Despite the increase in microwave power with ligand 3 from 35 W (entry 1) to 500 W (entry 5), the enantiomeric purity of product 2 was found to be almost constant. The phosphineoxazolines (7, 13, 14) yielded a better enantiomeric excess with microwave heating than was observed with ligand 3 and 4. With this class of ligands, attempts to truncate the reaction time by increasing the power was successful (entries 9–16). Complete conversions, high yields and high enantiomeric enrichment (up to 98% ee) was achieved. In particular, high stereose-lectivity and short reaction times were experienced with the tertiary butyl substituted phosphinooxazoline 13.

TABLE 1

Microwave-Induced Palladium Catalysed Asymmetric Alkylation of 1.

| entry | ligand | time (min) | power (W) | yield of 2ª (%) | ee (%) | absolute configuration |
|---|---|---|---|---|---|---|
| 1 | 3 | 15.0 | 35 | 99 | 65ᶜ | (R) |
| 2 | 3 | 7.5 | 70 | 99 | 64ᶜ | (R) |
| 3 | 3 | 3.5 | 120 | 99 | 63ᶜ | (R) |
| 4 | 3 | 3.0 | 250 | 99 | 65ᶜ | (R) |
| 5 | 3 | 2.0 | 500 | 99(95ᵇ) | 65ᶜ(63ᵈ) | (R) |
| 6 | 4 | 2.0 | 20 | 94 | 83ᶜ | (S) |
| 7 | 4 | 1.5 | 20 | 96 | 85ᶜ | (S) |
| 8 | 4 | 1.0 | 40 | 95(96ᵇ) | 83ᶜ(81ᵈ) | (S) |
| 9 | 7 | 2.0 | 30 | 92 | 94ᶜ | (S) |
| 10 | 7 | 1.0 | 120 | 96 | 92ᶜ | (S) |
| 11 | 7 | 0.5 | 500 | 90 | 91ᶜ | (S) |
| 12 | 13 | 5.0 | 10 | 88ᵉ | 98ᶜ | (S) |
| 13 | 13 | 1.0 | 90 | 99 | 96ᶜ | (S) |
| 14 | 13 | 0.5 | 120 | 97 | 94ᶜ | (S) |
| 15 | 13 | 0.25 | 500 | 99 | 91ᶜ | (S) |
| 16 | 14 | 1.0 | 120 | 95ᵇ | 93ᵈ | (R) |

Reactions were conducted under continuous microwave irradiation (2450 MHz) in sealed Pyrex tubes under an atmosphere of nitrogen.
ªDetermined by HPLC.
ᵇIsolated yield. >95% purity by HPLC.
ᶜDetermined by chiral HPLC.
ᵈDetermined by ¹H NMR.
ᵉConversion was only 90%.

As is apparent from Table 2, identical control experiments in acetonitrile at room temperature without microwave irradiation, provided high yields but very slow reaction rates with ligands 3, 4 and 7. Alkylation with ligand 3 was very slow and required three days for completion at room tempterature, a typical rate for N,N-ligands.

DMF, dichloromethane, 1,2-dichloroethane and benzotri-fluoride did not give the same good results as acetonitrile in this model system, irrespective of heating technique.

TABLE 2

Palladium Catalysed Asymmetric Alkylation of 1 at Room Temperature in Acetonitrile.

Ph—CH=CH—CH(OAc)—Ph (1) → (Pd(η³-C₃H₅)μ-Cl)₂, Ligand, H₂C(COOMe)₂, BSA, KOAc → Ph—CH=CH—CH*(CH(COOMe)₂)—Ph (2)

| entry | ligand | time (min) | yield of 2ª (%) | ee (%) | absolute configuration |
|---|---|---|---|---|---|
| 1 | 3 | 4300 | 99 | 77ᵇ (73ᶜ) | (R) |
| 2 | 4 | 60 | 97 | 87ᵇ (90ᶜ) | (S) |
| 3 | 7 | 1080 | 99ᶜ | 95ᵇ | (S) |

Reactions were conducted at 23° C. in sealed Pyrex tubes under nitrogen atmosphere. The reaction scale was 0.35 mmol in entry 1, 0.57 mmol in entry 2 and 0.44 mmol in entry 3.
ªIsolated yield. >95% purity by HPLC.
ᵇDetermined by chiral HPLC.
ᶜDetermined by ¹H NMR.

A comparison of entries 1–5 (Table 1) demonstrates that higher microwave power is needed for full conversion of the allyl acetate 1 in the short time reactions. Full conversion was encountered in 2.0 min at 500 W with 3 while 1.5 min was insufficient in this model example and a substantial amount of starting material remained unreacted in the latter case. (The reaction time could probably be reduced below 2.0 min with higher microwave power, but 500 W was the limit of the available apparatus.) With BINAP a power of 40 W was needed in the 1.0 min reactions with 4 (entry 8) but with lower power (30 W) starting material remained. Inter- Molybdenum In contrast to palladium, molybdenum has been shown to exercise different regioselectivity in allylic substitutions,[2a] as can be seen below. Therefore the achiral, unsymmetrical (E)-3-phenyl-2-propenyl methyl carbonate (10, (E)-cinnamyl methyl carbonate) was employed as substrate in an asymmetric allylic substitution procedure similar to the one described with palladium catalysis.

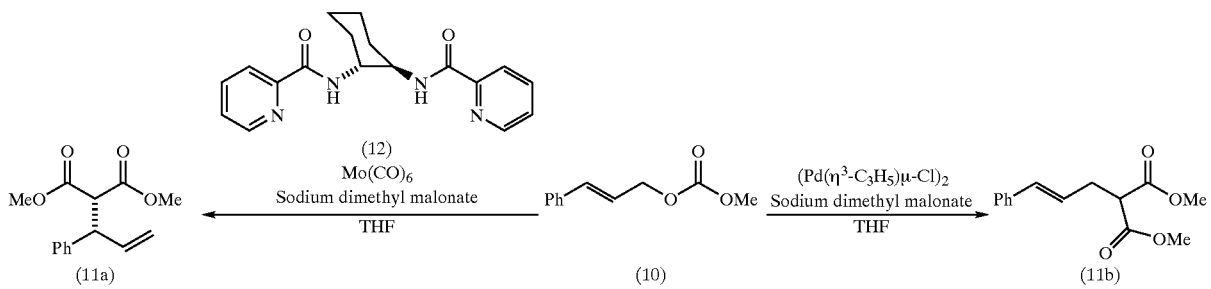

estingly and possibly reflecting a lability of the BINAP system as opposed to the quinolineoxazoline- and phosphinooxazoline systems, 50 W and above rendered a dramatic decrease in the conversion rate of 1 which might be attributed to an early collapse of the catalytic system. The P,N-class ligands showed even greater conversion rate and stability producing very high yields and enantiomeric purity in very short reaction times, as is demonstarated in Table 1 (entries 9–16). Furthermore, a comparison of entries 5, 6 and 9 reveals the much higher reactivity of catalytic systems comprising BINAP (4) or phosphinooxazolines as ligand, compared to catalysts generated from the quinolineoxazoline ligand 3.

Microwave energy transfer to an organic reaction in the liquid state occurs mainly by two mechanisms, namely dipole oscillation and ionic conduction.[4] in the reactions with the Pd-BINAP catalytic system, the contribution from the dipolar oscillation can be expected to be most predominant since both the final temperature and the ionic strength of the reaction mixture is relatively low. (Regarding the bulk of BSA and dimethyl malonate as non-ionized and all Pd as [Pd(ll)-LL-allyl]$^+$, the solution's ion strength depends only on the Pd-catalyst and dissolved KOAc (partly dissolved). Calculation yields I=0,014–0,026 for 3 and I=0,011–0,017 for 4 (lower limit: no KOAc dissolved, higher limit: all KOAc dissolved).) However, because of the very high energy densities employed in the fast reactions with 3 (or ligands 7, 13 and 14) as chiral ligand, it is highly probable that a temperature level is reached where the conductive losses are of great importance.[15] As a high microwave power and resulting fast heating gives less time for the sample to react at each given temperature, a decrease in reaction time has to be accompanied by a large increase in power. In addition, microwave absorbtion efficiency via dipole oscillation decreases with increasing temperature.[4,16] These two factors may explain the large increase in power necessary to obtain full conversion with 3 (or ligands 7, 13 and 14) as the reaction time is lowered. We assume that the impact of microwave flash-heating on the reaction rate is a consequence of fast and homogeneous in situ heating to relatively high temperatures.[16,17]

The reaction took place smoothly with dimethyl malonate in a catalytic system where (1R,2R)—N,N'-Bis-(2-pyridincarboxamide)-1,2-cyclohexane (12) was used as ligand. Using conventional oil-bath reflux conditions the reaction is reported to need several hours to reach completion.[3a] The transformation of 10 into 11a (see Figure above) was therefore chosen as a suitable molybdenum catalysed reaction for studies of microwave flash-heating. The alkylations were conducted essentially following the thermal procedure by Trost and Hachiya using the preformed sodium dimethyl malonate as base.[3a] An active molybdenum-ligand catalyst was prepared in situ by microwave flash-heating of a concentrated mixture of $Mo(CO)_6$ and 12. The microwave heating was performed with a single-mode cavity in sealed thin-walled Pyrex tubes.[13] The experiments were conducted in THF which is known to possess a sufficiently high dissipation factor (tan δ(rt)= 0.047)[4] to be efficiently heated under microwave irradiation. Note that the reactions were performed in air-atmosphere, in contrast to the reported procedure.[3a] One quick experiment using inert $N_2$-atmosphere showed no significant improvement. A similar experiment using reactive $O_2$-atmosphere did however give diminished catalytic activity, although a 20% yield of 11a was obtained after 1 min of microwave treatment (90 W). In Table 3 below, the microwave experiments with selected combinations of irradiation time and power that resulted in almost complete consumption of the starting material are summarised. The microwave-induced alkylations provided excellent yields, reaction rates and enantioselectivities. Determined regioselectivities were good, but optimisations are currently undertaken in our laboratory to reach excellent selectivities.

TABLE 3

Microwave-Induced Molybdenum Catalysed Asymmetric Alkylations of 10.

| Entry | Power × Time | Conversion (%) | Yield of 11a (%)[a] | Ratio (11a:11b) | ee (%)[b] |
|---|---|---|---|---|---|
| 1 | 30 W × 240 s | 91 | 83 | 11:1 | 98 |
| 2 | 60 W × 120 s | 93 | 85 | 11:1 | 98 |
| 3 | 90 W × 90 s | 95 | 88 | 12:1 | 98 |
| 4 | 120 W × 90 s | 98 | 89 | 10:1 | 98 |

TABLE 3-continued

Microwave-Induced Molybdenum Catalysed Asymmetric Alkylations of 10.

| Entry | Power × Time | Conversion (%) | Yield of 11a (%)[a] | Ratio (11a:11b) | ee (%)[b] |
|---|---|---|---|---|---|
| 5 | 250 W × 50 s | >99 | 93 | 10:1 | 98 |
| 6 | 500 W × 40 s | 95 | 47 | 5:1 | 98 |
| 7[c] | rt × 10800 s[c] | n.q.[c] | 70[d,c] | 49:1[c] | 99[c] |

Reactions were conducted under continuous microwave irradiation (2450 MHz) in sealed Pyrex tubes, except for entry 7, see below [c].
[a]: Yields determined by GC-MS with 2,3-dimethylnaphthalene as internal standard.
[b]: Experimentally determined ee:s by HPLC. Optical purity of 12 was ≦99%. If stereoinduction is assumed to be linear theoretical ee:s for 11a can be calculated to ≧99%.
[c]: Published results by Trost and Hachiya using conventional heating techniques.[3a]
[d]: Isolated yield.

A comparison of entries 1–6 (Table 3) demonstrates that higher microwave power is needed for full conversion of 10 in the short time reactions. This is indeed very common for all types of microwave heated reactions. Complete conversion was encountered in 50 s at 250 W.W.

As is apparent from Table 3, a non-microwave experiment in THF at room temperature provided high yield and ee, however only after long reaction time.[3a] Despite the reduction in recation time, from 3 h (entry 7) to 50 s (entry 5), the enantiomeric purity of 10 was found to be constant and very high. Only in the case of entry 6 incomplete consumption of the starting material and decomposition of the catalytic system was experienced. In fact, it was found that the small amount of product formed in entry 6 exhibited excellent enantiomeric purity. Based on these findings, one can speculate that the ligand is coordinating strongly to molybdenum, as is in agreement to reported calculations.[18] For discussions on the heating of the reaction mixture by microwaves, see reference 4.

EXPERIMENTAL SECTION

General Methods

The microwave heating was performed with a MicroWell 10 single-mode cavity from Labwell AB, SE-753 19 Uppsala, Sweden producing continuous irradiation at 2450 MHz (0–500 W).[19] The microwave-assisted reactions were performed in oven-dried, heavy-walled Pyrex tubes (8.0–8.5 mL, I=150 mm) for the palladium reactions and thin-walled Pyrex tubes (~10 mL, I=100 mm) for the molybdenum reactions. The tubes were sealed with screw caps or silicon septa. To secure a sufficient antenna function of the reaction mixture, the height of the liquid sample was >1.5 cm. Caution! When carrying out microwave heated reactions in closed vessels thermal stresses and/or high pressures (sometimes up to 20 atm.) can be generated. This applies in particular to reaction mixtures containing volatile substances or metal complexes (which if precipitated as finely divided metal particles can cause "thermal runaway"). Unless an appropriate pressure release device is used, e.g. a septum, this could result in an explosion. It is recommended to proceed with caution and keep the microwave reactor in an efficient fume hood.

Materials

Silicon septa (110.623-18), screw-caps with aperture (110.627-18) and screw-caps (110.626-18) were purchased from KEBO Lab AB. THF (Riedel-de Haén), PhMe (Merck), 2,3-dimetylnaphthalene (KEBO Lab AB), (+)-BINAP (4) (Strem), NaH (60% in mineraloil, Aldrich), dimethyl malonate (Aldrich), $Mo(CO)_6$(Aldrich), BSA (Lancaster), $(Pd(\eta^3-C_3H_5)\mu-Cl)_2$ (Lancaster/Aldrich), Cinnamyl alcohol (Aldrich), KOAc (Aldrich), and $Eu(hfc)_3$ (Aldrich) were used as received. The silica gel used was Merck Silica Gel 60. Acetonitrile and dichloromethane were distilled from $P_2O_5$ and stored over molecular sieves. Ligands 3,[9] 12,[20] 7,[20] 13,[21] 14,[21] rac-(E)-1,3-diphenyl-2-propenyl acetate (1)[22] and (E)-3-phenyl-2-propenyl methyl carbonate (10)[23] were prepared according to published procedures. 4-Methoxybenzonitrile was purified by recrystallization from ethanol/water followed by recrystallization from hexanes/toluene.

Palladium

General Procedure for Microwave-Induced Allylic Alkylation Reactions

Quinolineoxazoline (3) (56.9 mg, 0.207 mmol), (+)-(R)-BINAP (4) (42.7 mg, 0.069 mmol), phosphineoxazoline (7) (19.8 mg, 0.053 mmol), (13) (20.5 mg, 0.053 mmol), (14) (21.6 mg, 0.053 mmol) and $(Pd(\eta^3-C_3H_5)\mu-Cl)_2$(3: 25.3 mg, 0.069 mmol, 4: 12.4 mg, 0.034 mmol, 7,13,14: 8.1 mg, 0.022 mmol) were dissolved in dry acetonitrile (3: 7.2 mL, 4: 4.3 mL, 7, 13, 14: 7.0 mL ). The solution was degassed and stirred under nitrogen (3: 50° C., 2 h, 4: rt, 1 h, 7, 13,14: 50° C., 2 h). Bis(trimethylsilyl)acetamide (3: 2.11 g, 10.4 mmol, 4: 768 mg, 3.78 mmol, 7, 13,14: 2.71 g), 1,3-diphenyl-2-propenyl acetate (1) (3: 872 mg, 3.46 mmol, 4: 866 mg, 3.43 mmol, 7,13,14: 1121 mg, 4.44 mmol) and 4-methoxybenzonitrile (3: 1.19 9, 4: 1.18 9, 7,13,14: 1,51 g) were transferred with acetonitrile (3: 7.2 mL, 4: 4.3 mL, 7,13,14: 7.0 mL) to the reaction solution. A part of this solution (2.0 mL for each sample, total volume 3: 19.91 mL, 4: 12.08 mL, 7, 13, 14: 21.48 mL) was transferred to a heavy-walled Pyrex tube. KOAc (3: ~1.4 mg, ~0.014 mmol, 4: ~0.7 mg, ~0.007 mmol, 7,13,14: ~0.4 mg, ~0.004 mmol) and dimethyl malonate (3: 83 mg, 0.63 mmol, 4: 103 mg, 0.78 mmol,7,13,14: 176 mg, 1.33 mmol) were added and the reaction vessel was sealed with a silicon septum. The tube was positioned in the MicroWell 10 microwave reactor and the sample was irradiated with a suitable power for an appropriate time (see Table 1 for details). The reaction was quenched with water and the solvent was evaporated.

Liquid Chromatography

The residue from the reactions was taken up in isohexane/2-propanol (9/1, 30.0 mL). A small volume (3: 1.00 mL, 4: 0.60 mL, 7,13,14: 0.47 mL) of the diluted product mixture was filtered, dissolved in isohexane/2-propanol (97.5/2.5, 10.0 mL) and injected (20 1 μl) into a achiral Separon SGX (5 μm, 0.40 cm Ø×23 cm) HPLC-column. The fully resolved eluted peak of 2 ($t_R$=7.2 min) was collected as a squalemic mixture. The mobile phase consisted of degassed isohexane/2-propanol (97/3), 0.5 mL/min, and detection was carried out with a UV-monitor (254 nm, $t_R$(R)=20 min, $t_R$(S)=22 min). The yields were determined by mean values of 2–4 injections after a calibration curve made from pure 2 and 4-methoxybenzonitrile. All fractions containing product 2 were combined and analysed for enantiomeric purity using a chiral HPLC-column (DAICEL CHIRALCEL OD-H (0.46 cm Ø×25 cm)) with degassed isohexane/2-propanol (99/1), 0.5 mL/min as the mobile phase, and detection with a UV-monitor (254 nm). Reported ee values are mean values of 3–6 injections.

Alternatively the product was isolated. The acetonitrile was evaporated and the crude product passed through a silica gel column (MPLC) using a smooth exponential gradient of ethyl acetate in hexanes as eluent. All fractions containing product 2 were collected and the enantiomeric excess analyzed by $^1$H NMR spectroscopy (at rt, CDCl$_3$, 400 MHz) with 0.6 equiv Eu(hfc)$_3$ as chiral shift reagent, by comparison of the integrals of the signals from one of the methyl ester groups. The results are shown in Table 1. The reactions at room temperature (comparative examples) were carried out as described for the microwave-induced reactions but in absence of microwave irradiation. The results are shown in Table 2.

Molybdenum

General Procedure for Microwave-induced Allylic Alkylation Reactions

Two different stock solutions were prepared. "Solution-N" containing the nucloephile sodium dimetyl malonate in THF, was made by adding 60% NaH (0.60 g, 15 mmol) to 20 mL THF followed by dropwise addition of dimethyl malonate (1.6 mL, 10 mmol) to the stirred NaH-suspension during 10 min.[24] After complete addition of dimethyl malonate, "Solution-N" was allowed to react and cool down for 10 min. "Solution-S", containing the substrate, was prepared by dissolving the internal standard 2,3-dimethylnaphtalene (401 mg, 2.6 mmol) and substrate 10 (4.01 g, 21 mmol) in 20 mL THF. 125 µl of Ligand (12) (stock solution: 50 mg, 0.15 mmol, in 4.0 mL MeCN) and 125 µl Mo(CO)$_6$ (stock solution: 40 mg, 0.15 mmol, in 4.0 mL PhMe) were transferred to a thin-walled Pyrex-tube in the given order. Mild heating by a heat-gun was necessary to generate homogeneous supersaturated solutions.[25] The tube was sealed with a screw-cap and the precatalyst mixture was microwave-heated at 120 W for 5.0 min using the Microwell 10™ single-mode cavity to generate the active redbrown catalyst.[26] Next 1.00 mL of Solution-N and 0.50 mL of Solution-S was added to the catalyst-mixture in the given order and the tube was again sealed with a screw-cap. The tube was positioned in the MicroWell 10 microwave reactor and the sample was irradiated with a suitable power for an appropriate time (see Table 3 for details). After reaction the tube was cooled below the boiling point of THF in a water-bath at room temperature and then the reaction was quenched with 4 mL of 2 M HCl(aq).[27] The gelatinous orange reaction-mixture then turns deep-red, a colour which slowly fades away and has completely disappeared in a couple of days. The reaction-mixture was diluted with 4 mL of diethyl ether, filtered and analysed by GC-MS. The GC-MS yields were calculated using the internal standard.

Liquid Chromatography

The diethyl ether phase containing the reaction mixture (vide supra) was injected (20 µl) into an achiral Separon SGX (5 µm, 0.40 cm Ø×23 cm) HPLC—column. The second non-resolved eluted peak at t$_R$=7.0 min of 11a was collected as an impure squalemic mixture. The mobile phase consisted of degassed isohexane/2-propanol (96/4), 0.5 mL/min, and detection was carried out with a UV-monitor (220 nm). All fractions containing product 11a were combined and analysed for enantiomeric purity using a chiral HPLC-column (DAICEL CHIRALCEL OD-H (0.46 cm Ø×25 cm)) with degassed isohexane/2-propanol (99.5/0.5), 0.5 mL/min as the mobile phase, and detection with a UV-monitor (220 nm, t$_R$(R)=27 min, t$_R$(S)=29 min). Reported ee values are mean values of 6 injections.

REFERENCES AND NOTES ([1]) Trost, B. M.; Strege, P. E. J. Am. Chem. Soc. 1977, 99, 1649.

([2])For reviews, see: (a) Trost, B. M.; Van Vranken, D. L. Chem. Rev. 1996, 96, 365. (b) Shibasaki, M. in Advances in Metal-Organic Chemistry, Liebeskind, L. S., Ed.; JAI Press: Greenwich, 1996;

vol. 5, p 119. (c) Tsuji, J. Palladium Reagents and Catalysts; John Wiley: Chichester, 1995: p 290. (d) Pfaltz, A. In Steroselective Synthesis; Ottow, E., Schölikopf, K., Schulz, K.-G., Eds.; Springer-Verlag: Berlin, 1994; p 15. (e) Hayashi, T. In Catalytic Asymmetric Synthesis; Ojima, I., Ed.: VCH:

New York, 1993; p 325. (f) Frost, C. G.; Howarth, J.; Williams, J. M. J. Tetrahedron: Asymmetry 1992, 3, 1089. (g) Consiglio, G.; Waymouth, R. M. Chem. Rev. 1989, 89, 257.

([3]) (a) Trost, B. M.; Hachiya, I. J. Am. Chem. Soc. 1998, 1209, 1104. (b) Achiwa, I.; Yamazaki, A.; Achiwa, K. Synlett 1998, 45. (c) Gläser, B.; Kunz, H. Synlett 1998, 53. (d) Ahn, K. H.; Cho, C.-W; Park, J.; Lee, S. Tetrahedron: Asymmetry 1997, 8, 1179. (e) Chelucci, G. Tetrahedron: Asymmetry 1997, 8, 2667. (f) Nordstrom, K.; Macedo, E.; Moberg, C. J, Org. Chem. 1997, 62, 1604. (g) Zhang, W; Hirao, T.; Ikeda, I. Tetrahedron Lett. 1996, 37, 4545. (h) Andersson, P. G.; Harden, A.; Tanner, D.; Norrby, P.-O. Chem. Eur. J. 1995, 1, 12 (i) Valk, J.-M.; Claridge, T. D. W; Brown, J. M. Tetrahedron: Asymmetry 1995, 6, 2597. (j) Gamez, P.; Dunjic, B.; Fache, F.; Lemaire, M. Tetrahedron: Asymmetry 1995, 6, 1109. (k) von Matt. P.; Lloyd-Jones, G. C.; Minidis, A. B. E.; Pfaltz, A.; Macko, L.; Neuburger, M.; Zehnder, M.; Ruegger, H.; Pregosin, P. S. Helv. Chim. Acta 1995, 78, 265. (l) Wimmer, P.; Widhalm, M. Tetrahedron: Asymmetry 1995, 6, 657. (m) Kubota, H.: Koga, K. Tetrahedron Lett. 1994, 35, 6689. (n) Allen, J. V.; Coote, S. J.; Dawson, G. J.; Frost, C. G.; Martin, C. J.; Williams, J. M. J. J. Chem. Soc., Perkin Trans. 1 1994, 2065 (o) Kang, J.; Cho, W. O.; Cho, H. G. Tetrahedron: Asymmetry 1994, 5, 1347.

([4]) For reviews, see: (a) Mingos, D. M. P.; Baghurst, D. R. Chem. Soc. Rev. 1991, 20, 1. (b) Caddick, S. Tetrahedron 1995, 51, 10403. (c) Mingos, D. M. P.; Whittaker, A. G. Chemistry Under Extreme or Non-Classical Conditions; van Eldik, R.; Hubbard, C. D. Eds.; John Wiley & Sons, Inc. and Spektrum Akademischer Veriag: 1997; p 479. (d) Galema, S. A. Chem. Soc. Rev. 1997, 26, 233. (e) Langa, F.; de la Cruz, P.; de la Hoz, A.; Diaz-Ortiz, A.; Diez-Barra, E. Contemp. Org. Synth. 1997, 373. (f) Gabriel, C.; Gabriel, S.; Grant, E. H.; Halstead, B. S. J.; Mingos, D. M. P.; Chem. Soc. Rev, 1998, 27, 213. For Web pages devoted to microwave chemistry see: http://www.ed.ac.uk/~ah05/microwave.html ([5]) (a) Larhed, M.; Hallberg, A. J. Org. Chem. 1996, 61, 9582. (b) Diaz-Ortiz, A.; Prieto, P.; Vázquez, E. Synlett 1997, 269. (c) Li, J.; Mau. A. W. -H.; Strauss, C. R. J. Chem. Soc., Chem. Commun. 1997, 1275. (d) Wali, A.; Muthukumaru Pillai, S.; Satish, S. React. Kinet. Catal. Lett. 1997, 60, 189. (e) Garg, N.; Larhed, M.; Hallberg, A. J. Org. Chem. 1998, 63, 4158. (F) Olofsson, K.; Larhed, M.; Hallberg, A. J. Org. Chem., 1998, 63, 5076.

([6]) For microwave-assisted palladium-catalyzed cross-coupling reactions see: (a) Larhed, M.; Lindeberg, G.; Hallberg, A. Tetrahedron Lett. 1996, 37, 8219. (b) Larhed, M.; Hoshino, M.; Hadida, S.; Curran, D. P.; Hallberg, A. J. Org. Chem. 1997, 62, 5583. See also ref 5a.

([7]) Stone-Elander, S.; Elander, N. Appl. Radiat. Isot. 1993, 44, 889.

([8]) Noyori, R.; Takaya, H. Acc. Chem. Res. 1990, 23, 345.

([9]) Bremberg, U.; Rahm, F.; Moberg, K. Tetrahedron: Asymmetry, 1998, 9, 3437–3443.

Figure 2:
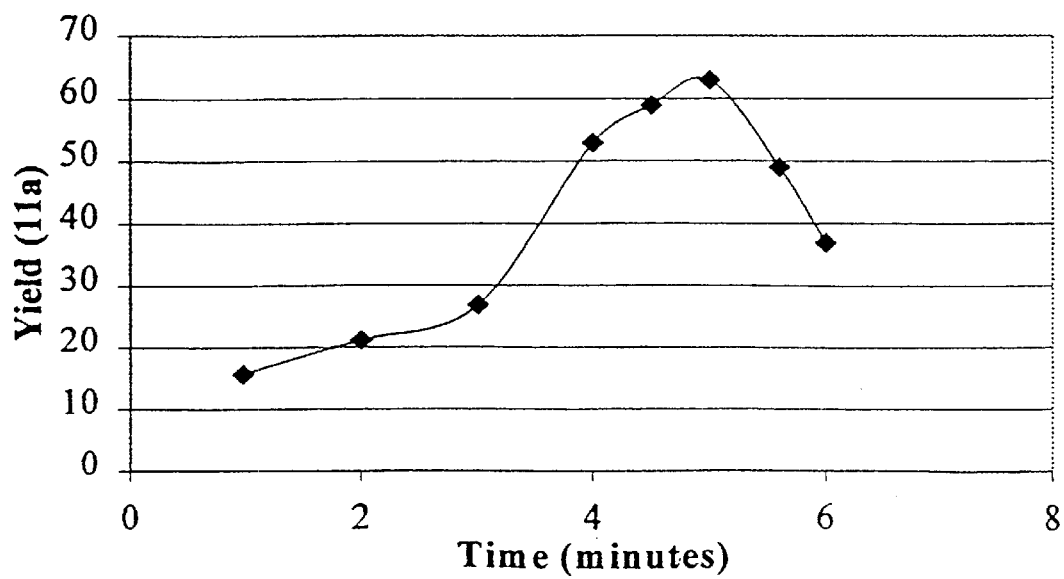
FIG. 2 illustrates a catalyst optimization.

(¹⁰) Von Matt, P., Pfaltz, A., Angew. Chem. Int. ed. Engl., 1993, 566; Allen, J. V.; Coote, S. J.; Dawson, G. J.; Frost, C. G.; Martin, C. J.; Williams, J. M. J. J. Chem. Soc., Perkin Trans. 1, 1994, 2065.
(¹¹) Trost, B. M.; Murphy, D. J. Organometallics 1985, 4, 1143.
(¹²) (a) Leutenegger, U.: Umbricht, G.; Fahrni, C.; von Matt, P.; Pfaltz, A. Tetrahedron 1992, 48, 2143. (b) Brown, J. M.; Hulmes, D. I.; Guiry, P. J. Tetrahedron 1994, 50. 4493.
(¹³) Closed Pyrex tubes can withstand higher pressures and higher temperatures compared to those which may safely be used with a Teflon vessel. Baghurst, D. R.; Mingos, D. M. P. J. Chem. Soc., Dalton Trans. 1992, 1151.
(¹⁴) (a) Stone-Elander, S.; Elander, N. Appl. Radiat. Isot. 1991, 42, 885. (b) Mingos, D. M. P.; Whittaker, A. G. J. Microwave Power and Electromag. Energy 1994, 29, 195.
(¹⁵) Zijistra, S.; de Groot, T J.; Kok, L. P.; Visser, G. M.; Vaalburg, W J. Org. Chem. 1993, 58, 1643.
(¹⁶) Strauss, C. R.; Trainor, R. W. Aust. J. Chem. 1995, 48, 1665.
(¹⁷) The very high reaction rate obtained under microwave heating in closed systems is probably arising from pressurized superheating, rather than being a result of a "magic" microwave effect. (a) Hájek, M. Collect. Czech. Chem. Commun. 1997, 62, 347. (b) Larhed, M. Ph.D. Thesis, Uppsala University, Oct. 1997.
(¹⁸) Nolan, S. P., de la Vega, R. L., Hoff, C. D., Organometatlics, 1986, 5, 2529.
(¹⁹) Stone-Elander, S. A.; Elander, N.; Thorell, J.-O.; Solas, G.; Svennebrink, J. J. Label. Cmpds. Radiopharm. 1994, 10, 949.
(²⁰) Barnes, D. J.; Chapman, R. L., J. Chem. Eng. Data, 1978, 23(4), 349.
(²¹) Koch, G., Lloyd-Jones, G. C., Loiseleur, O. Pfaltz, A., Prétôt R., Schaffner S., Schneider P., von Matt P., Recl. Trav. Chim. Pays-Bas, 1995, 206.
(²²) Auburn, P. R.; Mackenzie, P. B; Bosnich, B. J. Am. Chem. Soc. 1985, 107, 2033.
(²³) Lehmann, J., Lloyd-Jones, G. C., Tetrahedron, 1995, 8863
(²⁴) The solution might contain gelatinous solid parts. These parts seems to be aggregates of sodium dimetyl malonate. The aggregates seems not to influence the outcome of the reaction. Solution-N turns yellow on standing and yields get somewhat diminished. We choose always to use newly preperation Solution-N in our experiments.
(²⁵) In a control experiment using only the stock solution Of MO(CO)₆ as catalyst no conversion of 10 was detected. Thus, the ligand seems necessary for catalytic activity.
(²⁶) The reason for the high power and prolonged radiation time is the fact that the height of the liquid is very small, and thus the absorbtion of radiation in the sample is very inefficient. Below are shown two graphs. The first graph illustrates the heat generation at different sample heights of pure DMF under microwave irradiation (FIG. 1). The second graph illustrates the dependence of irradiation time on the generation of the active catalyst, as was measured by the yield in the subsequent reaction (FIG. 2).
FIG. 1: Sample height dependence: Height vs. maximal temperature in sample at 30 W×2 min.
FIG. 2: Catalyst optimisation; GC-MS yields of 11a vs. catalyst generation time: [MO(CO)₆+12] 120 W×t min→ [Reaction] 90 W×1 min.
(²⁷) The ligand 12 was completely recovered (≧90%) in a pure state by making the aqueous phase alkaline using 4 M NaOH and then extract it with CHCl₃, Et₂O or EtOA.

What is claimed is:

1. A method of performing a transition metal-catalysed asymmetric allylic substitution reaction, comprising the steps of:

a) preparing a reaction mixture comprising (i) an allylic substrate which includes the structural element C=C—C—X, where X is a leaving group, (ii) a catalyst complex which includes a transition metal and one or more chiral ligands, and (iii) a nucleophile; and b) exposing said reaction mixture to microwave energy from a controllable microwave source.

2. A method according to claim 1, wherein the reaction mixture is exposed to the microwave energy in a single mode microwave cavity.

3. A method according to claim 1, wherein the microwave energy has a frequency in the range of 300 MHz to 300 GHz.

4. A method according to claim 1, wherein the microwave energy is supplied to the reaction mixture at a power of 1–1000 W.

5. A method according to claim 1, wherein the microwave energy is supplied to the reaction mixture for a period of 1 s–1 h.

6. A method according to claim 1, wherein the transition metal of the catalyst complex is selected from cobalt (Co), copper (Cu), iridium (Ir), iron (Fe), manganese (Mn), molybdenum (Mo), nickel (Ni), osmium (Os), palladium (Pd), platinum (Pt), rhenium (Re), rhodium (Rh), ruthenium (Ru) or tungsten (W).

7. A method according to claim 1, wherein the ligand(s) of the catalyst complex is/are selected from $C_1$- or $C_2$-symmetrical ligands.

8. A method according to claim 7, wherein the ligand(s) is/are selected from:

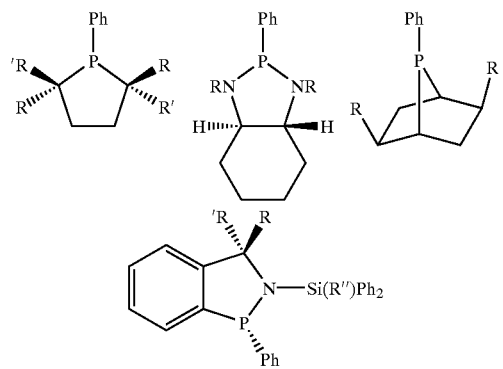

wherein Ph designates phenyl, R and R' each independently is hydrogen, $C_{1-10}$-alkyl or phenyl, and R" is selected from $C_{1-10}$-alkyl or phenyl.

9. A method according to claim 7, wherein the transition metal of the catalyst complex is palladium.

10. A method according to claim 7, wherein the transition metal is molybdenum and the ligand(s) is/are

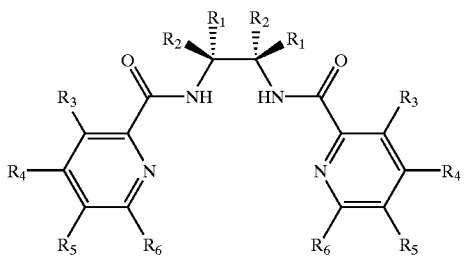

wherein $R_1$, $R_2$, $R_3$, $R_4$, $R_5$, and $R_{-6}$ each independently is hydrogen, $C_{1-6}$-alkyl, aryl, heteroaryl, hydroxy, alkoxy, di($C_{1-6}$-alkyl)amino, $C_{1-6}$-alkylthio, or tri($C_{1-6}$-alkyl and/or phenyl)silyl.

11. A method according to claim 7, wherein the catalyst complex is formed in situ.

12. A method according to claim 11, wherein the catalyst is generated by a microwave stimulated reaction between a catalyst precursor and free ligand(s).

13. A method according to claim 11, wherein the allylic substrate has the general formula

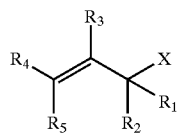

wherein $R_1$, $R_2$, $R_3$, $R_4$ and $R_5$ independently are selected from hydrogen, optionally substituted $C_{1-12}$-alkyl, optionally substituted aryl, optionally substituted heteroaryl, optionally substituted $C_{1-12}$-alkoxy, optionally substituted aryloxy, optionally substituted heteroaryloxy, tri($C_{1-6}$-alkyl and/or phenyl)silyl, or two of the substituents $R_1$, $R_2$, $R_3$, $R_4$ and $R_5$ together form a carbocyclic ring; and where X is a leaving group, and where X together with $R^1$ and the interconnecting atom may form an epoxide or an aziridine.

14. A method according to claim 13, wherein X is bromo, chloro, iodo, —OC(=O)R, —OCO$_2$R, —OPO(OR)$_2$, —OSOR, —OSO$_2$R, —OR, —OR$_2^+$, —SR$_2^+$, —SO$_2$R, —NR$_3^+$, —PR$_3^+$, —NO$_2$, or —CN, wherein R is hydrogen, $C_{1-10}$-alkyl, aryl, or heteroaryl.

15. A method according to claim 14, wherein X is —OAc.

16. A method according to claim 15, wherein the nucleophile is selected from

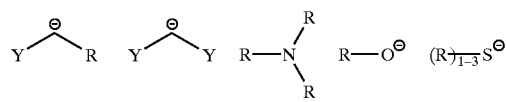

wherein Y is an electron withdrawing group and each R independently is hydrogen, $C_{1-12}$-alkyl, aryl-$C_{1-6}$-alkyl, aryl, heteroaryl, tri($C_{1-12}$-alkyl and/or phenyl)silyl, $C_{1-12}$-alkoxy, aryloxy, di($C_{1-20}$-alkyl) amino, $C_{1-12}$-alkylsulphonyl, or $C_{1-12}$-alkyloxycarbonyl.

17. A method according to claim 16, wherein the nucleophile is the deprotonated form of a compound selected from:

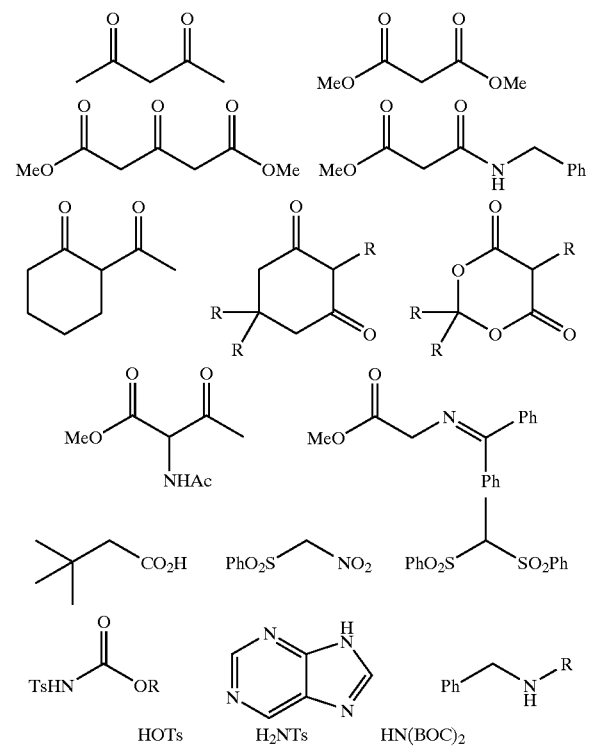

wherein each R independently is hydrogen, $C_{1-12}$-alkyl, aryl-$C_{1-6}$-alkyl, aryl, heteroaryl, tri($C_{1-12}$-alkyl and/or phenyl)silyl, $C_{1-12}$-alkoxy, aryloxy, di($C_{1-20}$-alkyl)amino, $C_{1-12}$-alkylsulphonyl, or $C_{1-12}$-alkyloxycarbonyl.

18. A method according to claim 16, wherein the nucleophile is generated in situ by reacting a nucleophile precursor with a strong base having a $pK_a$ in the range of 10–50.

19. A method according to claim 18, wherein the strong base is used in combination with a crown ether, a quarternary ammonium salt, or quaternary phosphonium salts.

20. A method according to claim 18, wherein the reaction mixture further comprises a solvent.

21. A method according to claim 20, wherein the solvent has a loss tangent of greater than about 0.04 at room temperature.

22. A method according to claim 20, wherein the solvent is acetonitrile, DMF, DMSO, NMP, water, MeOH, EtOH, benzonitrile, ethylene glycol, acetone, or THF.

23. A method according to claim 20, wherein the concentration of the allylic substrate in the solvent is in the range of $1 \times 10^{-3}$–2 M.

24. A method according to claim 20, wherein the concentration of the nucleophile in the solvent is in the range of $1 \times 10^{-3}$–2 M.

25. A method according to claim 20, wherein the concentration of the catalyst complex in the solvent is in the range of $1 \times 10^{-9}$–1 M.

26. A method according to claim 14, wherein the substrate is selected from

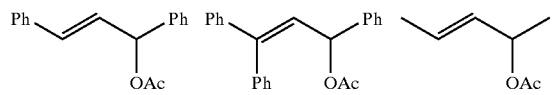

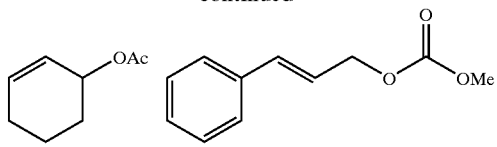

27. A method according to claim 13, wherein X is selected from the family —Y—C(=Y)Y—, where Y is independently O, N, or S.

28. A method according to claim 13, wherein at least one of $R_1$ to $R_5$ is aryl.

29. A method according to claim 1, wherein the ligand(s) of the catalyst complex has/have coordinating atoms selected from the group consisting of nitrogen (N), oxygen (O), sulphur (S), selenium (Se), phosphorus (P), tellurium (Te), antimony (Sb), carbon (C), and arsenic (As).

30. A method according to claim 1, wherein the ligand(s) of the catalyst complex is/are monodentate ligands.

31. The method according to claim 1, wherein the ligands (s) of the catalyst complex is/are bidentate ligands.

32. A method according to claim 31, wherein the ligand(s) is/are nitrogen based ligands selected from

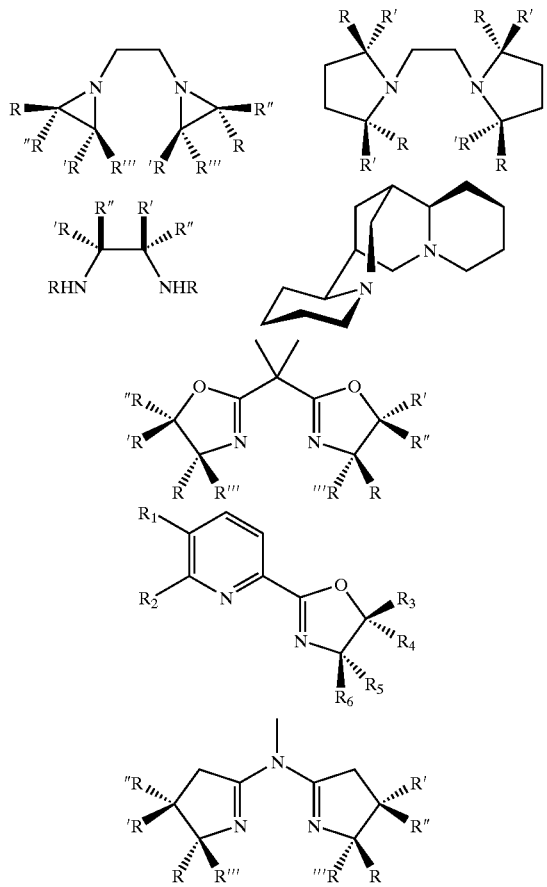

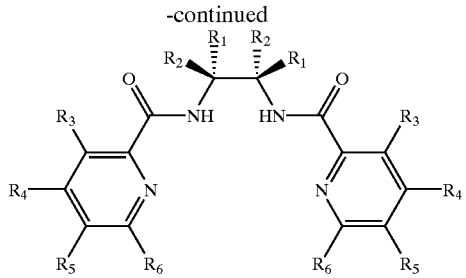

wherein R, R', R", and R'" each independently is hydrogen, $C_{1-10}$-alkyl or phenyl, and $R_1$, $R_2$, $R_3$, $R_4$, $R_5$ and $R_6$ each independently is hydrogen, $C_{1-10}$-alkyl or phenyl, where $R_1$ and $R_2$ together with the interconnecting atoms may form a benzene ring.

33. A method according to claim 31, wherein the ligand(s) is/are phosphorus based ligands selected from

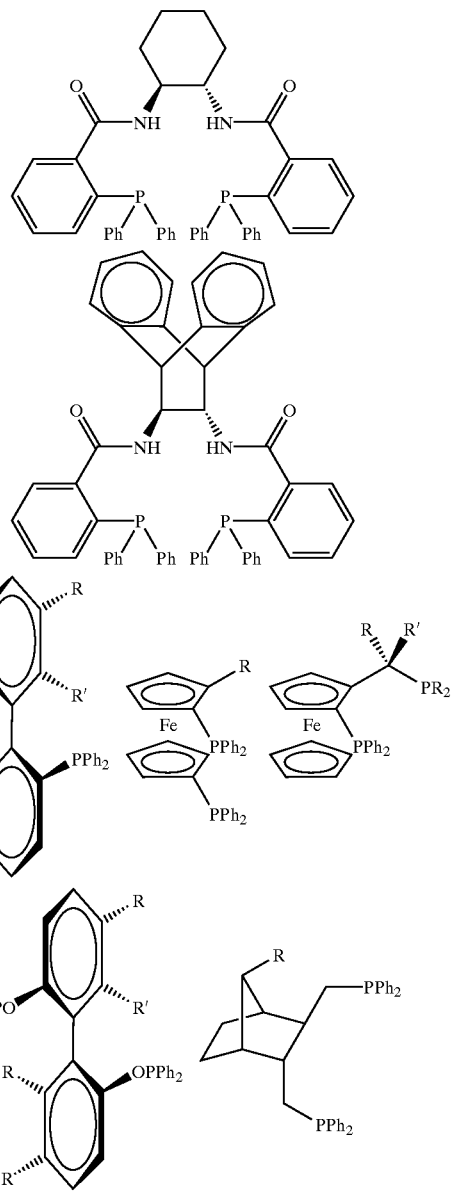

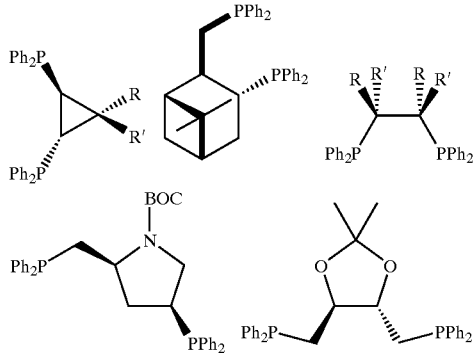
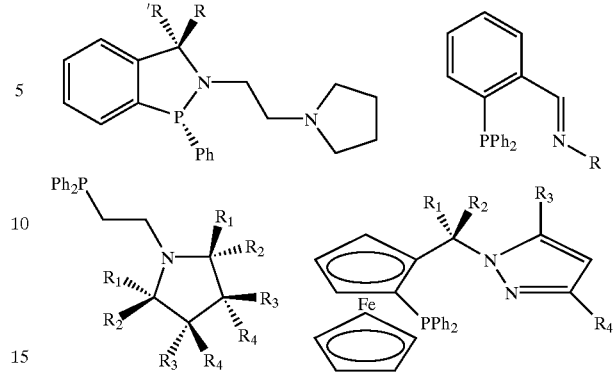

wherein Ph designates phenyl and R and R' each independently is hydrogen, $C_{1-6}$-alkyl, or phenyl, where R and R' together with the interconnecting atoms may form a carbocyclic ring.

34. A method according to claim 31, wherein the ligand(s) is/are phosphorus/nitrogen based ligands selected from

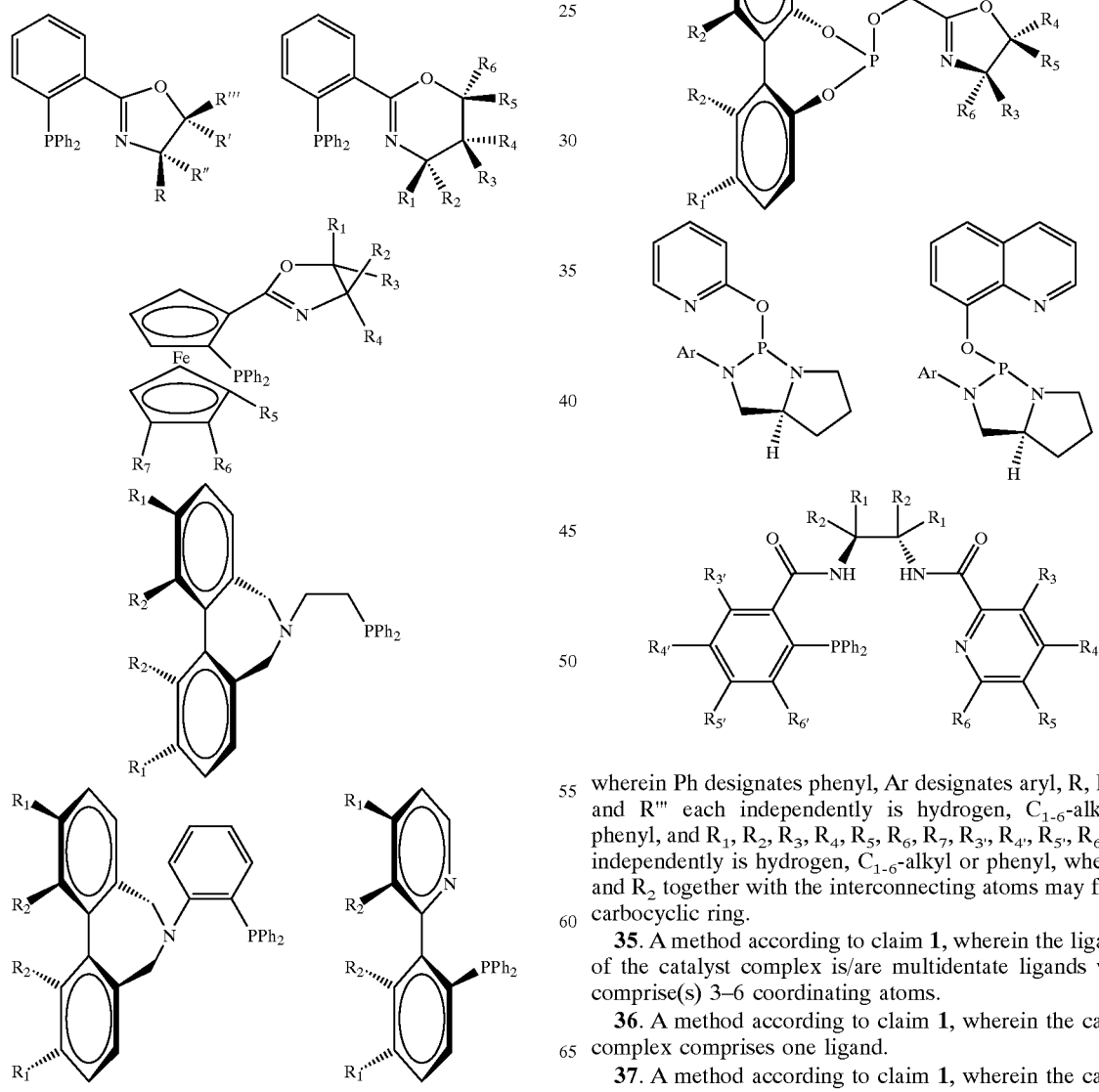

wherein Ph designates phenyl, Ar designates aryl, R, R', R" and R''' each independently is hydrogen, $C_{1-6}$-alkyl or phenyl, and $R_1$, $R_2$, $R_3$, $R_4$, $R_5$, $R_6$, $R_7$, $R_{3'}$, $R_{4'}$, $R_{5'}$, $R_{6'}$ each independently is hydrogen, $C_{1-6}$-alkyl or phenyl, where $R_1$ and $R_2$ together with the interconnecting atoms may form a carbocyclic ring.

35. A method according to claim 1, wherein the ligand(s) of the catalyst complex is/are multidentate ligands which comprise(s) 3–6 coordinating atoms.

36. A method according to claim 1, wherein the catalyst complex comprises one ligand.

37. A method according to claim 1, wherein the catalyst complex comprises more than one ligand.

38. A method according to claim 1, wherein the reaction mixture does not comprise a solvent.

39. A method according to claim 1, wherein the molar ratio between the nucleophile and the allylic substrate is in the range of 1000:1–1:1000.

40. A method according to claim 1, wherein the molar ratio between the catalyst complex and the allylic substrate is in the range of $1:1-1:1\times10^9$.

41. A method according to claim 1, wherein the allylic substitution reaction yields an enantiomeric excess (ee) of one of the theoretically possible reaction products.

42. A method according to claim 41, wherein the enantiomeric excess (ee) is >60%.

43. A method according to claim 41, wherein the allylic substitution reaction yields a diastereomeric excess (de) of one of the theoretically possible reaction products.

44. A method according to claim 43, wherein the diasteromeric excess (de) is >60%.

45. A method according to claim 1, wherein the allylic substrate and/or the nucleophile have been enriched with a radio-isotope.

46. A method according to claim 45, wherein the radio-isotope is a positron emitting isotope.

47. A method for preparing a compound library of products of a transition metal-catalysed allylic substitution reaction, comprising the steps of:
   a) preparing a reaction mixture comprising (i) n different species of allylic substrates which include the structural element C=C—C—X, where X is a leaving group, (ii) a catalyst complex which includes a transition metal and one or more ligands, and (iii) m different nucleophiles, wherein n is an integer in the range of 1–25 and m is an integer in the range of 1–10, with the proviso that the product n×m is at least 2; and
   b) exposing said reaction mixture to microwave energy from a controllable microwave source.

48. A method according to claim 47, wherein the reaction mixture is exposed to the microwave energy in a single mode microwave cavity.

49. A method according to claim 47, wherein the microwave energy has a frequency in the range of 300 MHz to 300 GHz.

50. A method according to claim 47, wherein the microwave energy is supplied to the reaction mixture at a power of 1–1000 W.

51. A method according to claim 47, wherein the microwave energy is supplied to the reaction mixture for a period of 1 s–1 h.

52. A method according to claim 47, wherein the transition metal of the catalyst complex is selected from cobalt (Co), copper (Cu), iridium (Ir), iron (Fe), manganese (Mn), molybdenum (Mo), nickel (Ni), osmium (Os), palladium (Pd), platinum (Pt), rhenium (Re), rhodium (Rh), ruthenium (Ru) or tungsten (W).

53. A method according to claim 47, wherein the ligand(s) of the catalyst complex is/are selected from chiral ligands.

54. A method according to claim 47, wherein the ligand(s) of the catalyst complex is/are selected from $C_1$- or $C_2$-symmetrical ligands.

55. A method according to claim 47, wherein the ligand(s) of the catalyst complex has/have coordinating atoms selected from the group consisting of nitrogen (N), oxygen (O), sulphur (S), selenium (Se), phosphorus (P), tellurium (Te), antimony (Sb), carbon (C), and arsenic (As).

56. A method according to claim 47, wherein the ligand(s) of the catalyst complex is/are monodenate ligands.

57. A method of performing a microwave promoted allylic substitution reaction which comprises the following steps:
   a) preparing a reaction mixture comprising: (i) an allylic substrate which includes the structural element C=C—C—X, where X is a leaving group, (ii) a transition metal-catalyst complex including a $C_1$- or $C_2$-symmetrical chiral ligand, and (iii) a nucleophile; and
   b) exposing said reaction mixture to microwave energy from a controllable microwave source.

* * * * *